(12) United States Patent
Guo et al.

(10) Patent No.: US 7,550,467 B2
(45) Date of Patent: Jun. 23, 2009

(54) BICYCLIC COMPOUNDS AS SELECTIVE MELANIN CONCENTRATING HORMONE RECEPTOR ANTAGONISTS FOR THE TREATMENT OF OBESITY AND RELATED DISORDERS

(75) Inventors: Tao Guo, Dayton, NJ (US); Huizhong Gu, Monmouth Junction, NJ (US); Douglas Walsh Hobbs, Yardley, PA (US)

(73) Assignee: Schering Corporation, Kenilworth, NJ (US)

( * ) Notice: Subject to any disclaimer, the term of this patent is extended or adjusted under 35 U.S.C. 154(b) by 560 days.

(21) Appl. No.: 11/247,635

(22) Filed: Oct. 11, 2005

(65) Prior Publication Data

US 2006/0111360 A1 May 25, 2006

Related U.S. Application Data

(60) Provisional application No. 60/617,873, filed on Oct. 12, 2004.

(51) Int. Cl.
*A61K 31/497* (2006.01)
(52) U.S. Cl. .................. 514/252.12; 544/360; 546/348; 585/25
(58) Field of Classification Search ............ 514/252.12; 544/360; 546/348; 585/25
See application file for complete search history.

(56) References Cited

U.S. PATENT DOCUMENTS

2001/0041700 A1 * 11/2001 Bekkali et al. ............ 514/224.8

FOREIGN PATENT DOCUMENTS

| WO | WO 02/057233 | * | 7/2002 |
| WO | WO 03/007888 | * | 1/2003 |
| WO | WO 03/047568 | * | 6/2003 |
| WO | WO 2004/037777 | * | 5/2004 |

* cited by examiner

Primary Examiner—James O Wilson
Assistant Examiner—Douglas M Willis
(74) Attorney, Agent, or Firm—Palaiyur S. Kalyanaraman

(57) ABSTRACT

The present invention discloses compounds of Formula I

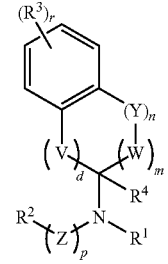

Formula I wherein V, W, Y, Z, $R^1$, $R^2$, $R^3$, $R^4$, d, m, n, p and r are herein defined, said compounds being novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes. An illustrative compound is shown below:

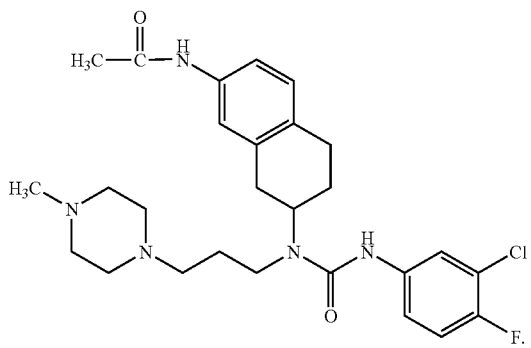

19 Claims, No Drawings

BICYCLIC COMPOUNDS AS SELECTIVE MELANIN CONCENTRATING HORMONE RECEPTOR ANTAGONISTS FOR THE TREATMENT OF OBESITY AND RELATED DISORDERS

CROSS REFERENCE TO RELATED APPLICATIONS

This application claims the benefit of U.S. Provisional Application No. 60/617,873 filed on Oct. 12, 2004.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions comprising one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an Example of the latter being an MCH antagonist. Further, MCH receptor antagonists may also be useful in the treatment of depression and/or anxiety. Borowksy et al., *Nature Medicine*, 8, pp. 825-830 (1 Aug. 2002).

WO 03/047568 discloses compounds having MCH antagonistic activity. A desired goal is to find compounds that have low Ki values and fewer side effects.

SUMMARY OF THE INVENTION

In one embodiment, this invention provides novel bicyclic compounds having MCH antagonist activity. These compounds are represented by Formula I

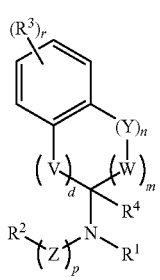

or a pharmaceutically acceptable salt thereof wherein:

V is —C($R^5R^6$)—;
W is —C($R^7R^8$)—;
Y is independently selected at each occurrence thereof and is —$CH_2$—, —O—, —S—, —S(O)—, —$S(O)_2$— or —N($R^{20}$)—;
Z is —C($R^9R^{10}$)—;
$R^1$ is $R^1$ is

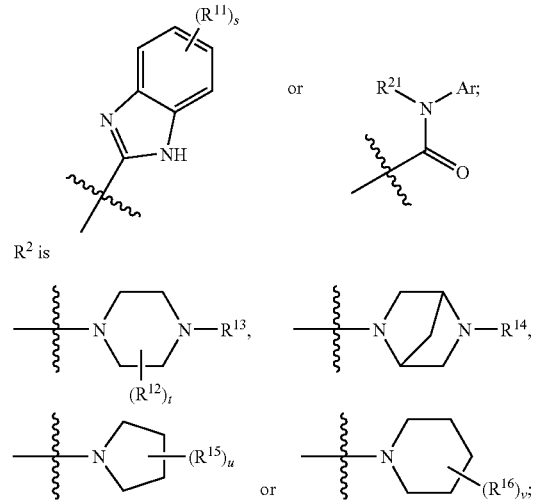

Ar is $(R^{19})_q$-substituted aryl or $(R^{19})_q$-substituted heteroaryl;

$R^3$ is independently selected at each occurrence thereof from the group consisting of: H, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, keto, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), -alkyl-$NR^{17}R^{18}$, —C(=O)$NR^{17}R^{18}$, —$NR^{17}R^{18}$, —NHC(=O)$R^{17}$, —NHC(=O)$OR^{17}$, —NHC(=O)$NR^{17}R^{18}$, —NHS$(O)_2$ $R^{17}R^{18}$, —NHS$(O)_2NR^{17}$, —NHS$(O)_2NR^{17}R^{18}$, —S(O)$R^{17}$, —S$(O)_2R^{17}$ and —S$(O)_2NR^{17}R^{18}$;

or two $R^3$ moieties on adjacent carbons can be linked together to form a 4 to 6 membered cycloalkyl or 4 to 6 membered heterocyclyl group, with the proviso that there are no adjacent oxygen or sulfur atoms present in the heterocyclyl group, wherein the cycloalkyl and heterocyclyl groups are fused to the ring carbons to which $R^3$ is attached;

$R^4$ is —H, alkyl, alkenyl, alkynyl, cycloalkyl or cycloalkylalkyl;

$R^5$, $R^6$, $R^7$, $R^8$, $R^9$ and $R^{10}$ are each independently selected at each occurrence thereof and are each independently —H or alkyl;

$R^{11}$ is independently selected at each occurrence thereof from the group consisting of: H, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—$NH_2$, —C(=NH)—$NH_2$, —C(=NH)—NH(alkyl), -alkyl- $NR^{17}R^{18}$, —C(=O)$NR^{17}R^{18}$, —$NR^{17}R^{18}$, —NHC(=O)$R^{17}$, —NHC(=O)$OR^{17}$, —NHC(=O)$NR^{17}R^{18}$, —NHS(O)$_2$$R^{17}R^{18}$, —NHS(O)$_2$$R^{17}$, —NHS(O)$_2$$NR^{17}R^{18}$, —S(O)$_2$$NR^{17}R^{18}$, and —S(O)$_2$$NR^{17}R^{18}$;

or two $R^{11}$ moieties on adjacent carbons can be linked together to form

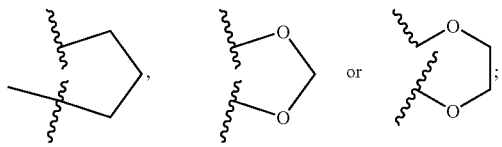

$R^{12}$ is independently selected at each occurrence thereof from the group consisting of: H, alkyl, cycloalkyl, alkoxyalkyl, hydroxyalkyl and cycloalkoxyalkyl;

$R^{13}$ is H, alkyl, aryl, heteroaryl, alkoxyalkyl, hydroxyalkyl, acyl, alkoxycarbonyl, cycloalkoxyalkyl, carbamoyl, arylsulfonyl, alkylsulfonyl or —CN;

$R^{14}$ is H, alkyl, aryl, heteroaryl, acyl, alkoxyalkyl, hydroxyalkyl, alkoxycarbonyl, cycloalkoxyalkyl, carbamoyl, arylsulfonyl, alkylsulfonyl or —CN;

$R^{15}$ is independently selected at each occurrence thereof from the group consisting of: H, —OH, halogen, alkyl, alkoxy, aryl, heteroaryl, alkoxyalkyl, hydroxyalkyl, aryloxy, cycloalkoxyalkyl, and heteroaryloxy;

$R^{16}$ is independently selected at each occurrence thereof from the group consisting of: H, —OH, halogen, alkyl, alkoxy, aryl, heteroaryl, alkoxyalkyl, hydroxyalkyl, aryloxy, cycloalkoxyalkyl, and heteroaryloxy;

$R^{17}$ and $R^{18}$ are each independently selected at each occurrence thereof and are each independently H, alkyl, cycloalkyl, aryl, heteroalkyl and heteroarylalkyl;

$R^{19}$ is independently selected at each occurrence thereof from the group consisting of: H, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), —$NR^{17}R^{18}$, -alkyl-$NR^{17}R^{18}$, —C(=O)$NR^{17}R^{18}$, —NHC(=O)$R^{17}$, —NHC(=O)$OR^{17}$, —NHC(=O)$NR^{17}R^{18}$, —NHS(O)$_2$$R^{17}R^{18}$, —NHS(O)$_2$$R^{17}$, —NHS(O)$_2$$NR^{17}R^{18}$, —S(O)$_2$$NR^{17}R^{18}$, and —S(O)$_2$$NR^{17}R^{18}$;

$R^{20}$ is independently selected at each occurrence thereof and is H, alkyl, cycloalkyl, aryl, heteroaryl or heteroaralkyl;

$R^{21}$ is —H or alkyl;

d is 0, 1 or 2;

m, q and u are each independently 1, 2 or 3, with the proviso that sum of m, n and d is not greater than 4;

n is 0 or 1;

p is 2, 3 or 4;

r, s and v are each independently 1, 2, 3 or 4; and t is 1 or 2.

This invention is also directed to pharmaceutical compositions for the treatment of metabolic disorders such as obesity, those disorders associated with obesity and eating disorders such as hyperphagia, using at least one compound of Formula I, or, salts solvates or esters thereof. In one aspect, this invention is directed to the method of treatment of metabolic disorder(s) such as obesity, and/or eating disorder(s) such as hyperphagia using the compound of Formula I or salts or solvates thereof.

Another embodiment includes a method of treating an eating disorder which comprises administering to a mammal in need of such treatment an amount of a first compound, said first compound being a compound according to Formula I or, salts, solvates or esters thereof; and a second compound, said second compound being an antiobesity and/or anorectic agent wherein the amounts of the first and second compounds result in the desired therapeutic effect.

In another aspect, this invention is directed to pharmaceutical compositions for the treatment of obesity which comprise an obesity treating amount of at least one compound of Formula I, or a pharmaceutically acceptable, or, salts, solvates or esters thereof of said compound and a pharmaceutically acceptable carrier.

DETAILED DESCRIPTION

The present invention relates to compounds that are represented by structural Formula I, or a pharmaceutically acceptable, or salts, solvates or esters thereof, wherein the various moieties are as described above.

One aspect of the invention include those compounds of Formula I wherein $R^1$ is

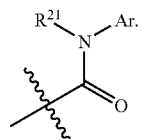

Another aspect of the invention includes those compounds of Formula I wherein $R^2$ is

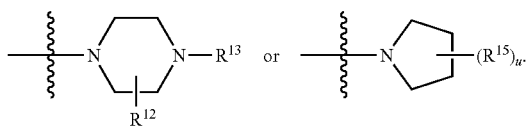

Another aspect of the invention includes those compounds of Formula I wherein $R^3$ is independently selected from the group consisting of: H, halogen, alkyl, alkoxy, —NH$_2$ —CN, —NO$_2$, —NHS(O)$_2$$R^{17}$, —NHC(=O)$NR^{17}R^{18}$, —S(O)$_2$$R^{17}$ and —NHC(=O)$R^{17}$;

or two $R^3$ moieties on adjacent carbons are linked together to form

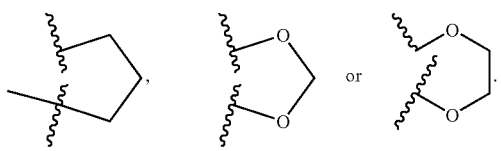

Another aspect of the invention includes those compounds of Formula I wherein $R^3$ is independently selected from the group consisting of: H, halogen, alkyl, alkoxy, —NHC(=O)alkyl, —NO$_2$, NH$^2$, —CN, —NHS(O)$_2$alkyl, —NHC(=O)NHalkyl and —S(O)$_2$alkyl.

Another aspect of the invention includes those compounds of Formula I wherein $R^4$ is H.

Another aspect of the invention includes those compounds of Formula I wherein $R^5$ is H.

Another aspect of the invention includes those compounds of Formula I wherein $R^6$ is H.

Another aspect of the invention includes those compounds of Formula I wherein $R^7$ is H.

Another aspect of the invention includes those compounds of Formula I wherein $R^8$ is H.

Another aspect of the invention includes those compounds of Formula I wherein at each occurrence $R^9$ is H.

Another aspect of the invention includes those compounds of Formula I wherein at each occurrence $R^{10}$ is H.

Another aspect of the invention includes those compounds of Formula I wherein $R^{11}$ is independently selected at each occurrence thereof from the group consisting of: H, halogen and —$CF_3$.

Another aspect of the invention includes those compounds of Formula I wherein $R^{21}$ is H.

Another aspect of the invention includes those compounds of Formula I wherein $R^{12}$ is independently selected at each occurrence thereof and is H or alkyl.

Another aspect of the invention includes those compounds of Formula I wherein $R^{13}$ is H, alkyl, acyl, alkoxycarbonyl, carbamoyl, arylsulfonyl or —CN.

Another aspect of the invention includes those compounds of Formula I wherein $R^{13}$ is H, alkyl or alkoxycarbonyl.

Another aspect of the invention includes those compounds of Formula I wherein $R^{14}$ is H, alkyl, alkoxyalkyl or hydroxyalkyl.

Another aspect of the invention includes those compounds of Formula I wherein $R^{15}$ is independently selected at each occurrence thereof from the group consisting of: H, —OH, alkyl or alkoxycarbonyl.

Another aspect of the invention includes those compounds of Formula I wherein $R^{16}$ is independently selection at each occurrence thereof from the group consisting of: H, —OH, alkyl, alkoxyalkyl or hydroxyalkyl.

Another aspect of the invention includes those compounds of Formula I wherein $R^{17}$ is independently selected at each occurrence thereof from the group consisting of: H, —$CH_3$, —$CH(CH_3)_2$ or $CH_2CH_3$.

Another aspect of the invention includes those compounds of Formula I wherein $R^{18}$ is independently selected at each occurrence thereof from the group consisting of: H, —$CH_3$, —$CH(CH_3)_2$ or —$CH_2CH_3$.

Another aspect of the invention includes those compounds of Formula I wherein Ar is $(R^{19})_q$-substituted aryl or $(R^{19})_q$-substituted heteroaryl wherein the aryl and heteroaryl are six membered rings.

Another aspect of the invention includes those compounds of Formula I wherein $R^{19}$ is independently selected at each occurrence thereof from the group consisting of: H, halogen, —$CF_3$ and —CN.

Another aspect of the invention includes those compounds of Formula I wherein d is 1.

Another aspect of the invention includes those compounds of Formula I wherein m is 1 or 2.

Another aspect of the invention includes those compounds of Formula I wherein n is 1.

Another aspect of the invention includes those compounds of Formula I wherein p is 2 or 3.

Another aspect of the invention includes those compounds of Formula I wherein q is 2.

Another aspect of the invention includes those compounds of Formula I wherein r is 1 or 2.

Another aspect of the invention includes those compounds of Formula I wherein s is 1 or 2.

Another aspect of the invention includes those compounds of Formula I wherein t is 2.

Another aspect of the invention includes those compounds of Formula I wherein u is 1 or 2.

Another aspect of the invention includes those compounds of Formula I wherein v is 1 or 2.

Another aspect of the invention includes those compounds of Formula I wherein Y is $CH_2$ or O.

Additional aspects of the invention include those compounds of Formula 1 having the general structure represented by structural Formula 2:

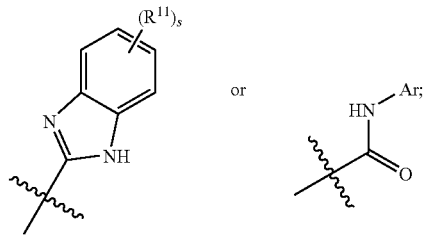

Formula 2 or a pharmaceutically acceptable or, salts, solvates or esters thereof.

Additional aspects of the invention include those compounds of Formula 1 having the general structure represented by structural Formula 2 wherein:

$R^1$ is

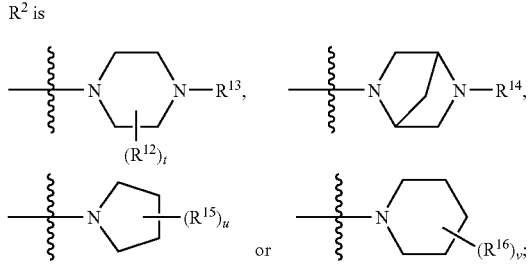

$R^2$ is

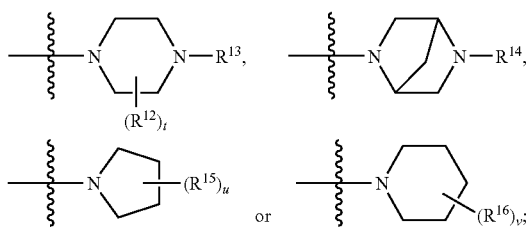

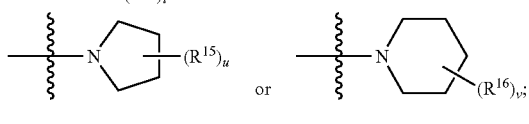

$R^3$ is independently selected at each occurrence thereof from the group consisting of: halogen, —CN, —$NO_2$ and —NHC(=O)$R^{17}$;

$R^{11}$ is independently selected at each occurrence thereof from the group consisting of: H, halogen and —$CF_3$;

$R^{12}$ is independently selected at each occurrence thereof from the group consisting of: H or alkyl;

$R^{13}$ is H, alkyl, acyl, alkoxycarbonyl, carbamoyl, arylsulfonyl or —CN;

$R^{14}$ is H, alkyl, alkoxyalkyl or hydroxyalkyl;

$R^{15}$ is independently selected at each occurrence thereof from the group consisting of: H, —OH, alkoxy, alkoxyalkyl and hydroxyalkyl;

$R^{16}$ is independently selected at each occurrence thereof from the group consisting of: H, —OH, alkyl, alkoxy, alkoxyalkyl and hydroxyalkyl;

$R^{17}$ is independently selected at each occurrence thereof and is H or alkyl;

Ar is $(R^{19})_q$-substituted aryl or $(R^{19})_q$-substituted heteroaryl wherein the aryl and heteroaryl are six membered rings;

$R^{19}$ independently selected at each occurrence thereof from the group consisting of: H, halogen, —$CF_3$ and —CN;

d is 0 or 1;

m is 1 or 2;

n is 0 or 1 and when n is 1, Y is $CH_2$ or O;

p is 2 or 3;

q is 2; and r, s, t, u and v are each independently 1 or 2.

Additional aspects of the invention include those compounds of Formula 1 having the general structure represented by structural Formula 3:

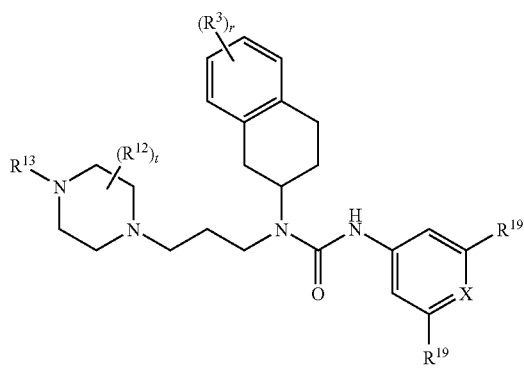

Formula 3 or a pharmaceutically acceptable salts, solvates or esters thereof wherein X is CH, CF or N.

Additional aspects of the invention include those compounds of Formula 1 having the general structure represented by structural Formula 3 wherein:

$R^3$ is independently selected at each occurrence thereof from the group consisting of: H, halogen, alkyl, alkoxy, —$NH_2$—CN, —$NO_2$, —$NHS(O_2)R^{17}$, —$NHC(=O)NR^{17}R^{18}$, —$S(O_2)R^{17}$ and —$NHCOR^{17}$;

$R^{12}$ is independently selected at each occurrence thereof from the group consisting of: H and alkyl;

$R^{13}$ is H, alkyl or —C(=O)Oalkyl;

$R^{19}$ is independently selected at each occurrence thereof and is —H, —$CF_3$ or halogen and further wherein one embodiment, $R^{19}$ is not —$CF_3$ at each occurrence;

X is CF or N; and r and t are 2.

Additional aspects of the invention include those compounds of Formula 1 having the general structure represented by structural Formula 4:

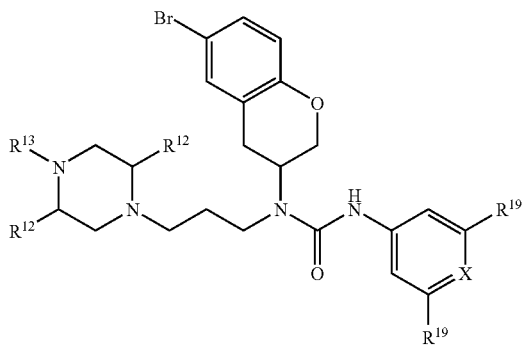

Formula 4 or a pharmaceutically acceptable salts, solvates or esters thereof, wherein X is CH, CF or N.

Additional aspects of the invention include those compounds of Formula 1 having the general structure represented by structural Formula 4 wherein:

$R^{12}$ is independently selected at each occurrence thereof from the group consisting of: H and alkyl;

$R^{13}$ is H, alkyl or —C(=O)Oalkyl;

$R^{19}$ is independently selected at each occurrence thereof and is H, —$CF_3$ or halogen and further wherein one embodiment, $R^{19}$ is not —$CF_3$ at each occurrence; and X is CF or N.

Additional aspects of the invention include those compounds of Formula 1 having the general structure represented by structural Formula 5:

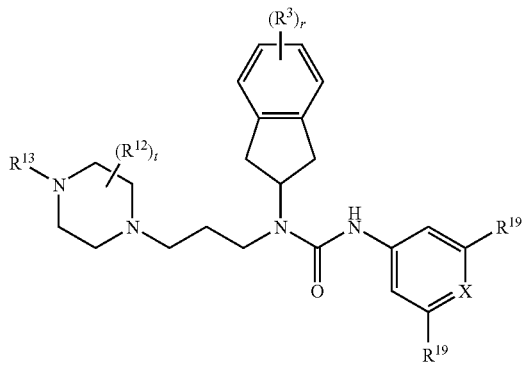

Formula 5 or a pharmaceutically acceptable salts, solvates or esters thereof wherein X is CH, CF or N.

Additional aspects of the invention include those compounds of Formula 1 having the general structure represented by structural Formula 5 wherein:

$R^3$ is independently selected from the group consisting of: H, halogen, alkyl, alkoxy, —$NH_2$—CN, —$NO_2$, —$NHS(O_2)R^{17}$, —$NHC(=O)NR^{17}R^{18}$, —$S(O_2)R^{17}$ and —$NHC(=O)R^{17}$;

$R^{12}$ is independently selected at each occurrence thereof from the group consisting of: H and alkyl;

$R^{13}$ is H, alkyl or —C(=O)Oalkyl;

$R^{19}$ is independently selected at each occurrence thereof and is —H, —$CF_3$ or halogen and further wherein one embodiment, $R^{19}$ is not —$CF_3$ at each occurrence;

X is CF or N; and r and t are 2.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. Aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl" means an alkoxy-alkyl group in which the alkoxy and alkyl groups are as previously described. Non-limiting examples of suitable alkoxyalkyl groups include methoxymethyl and ethoxymethyl. The bond to the parent moiety is through the alkyl group.

"Alkoxycarbonyl" means an alkyl-O—C(O)— group in which the alkyl group is as previously described. Non-limiting examples of suitable alkoxycarbonyl groups include methoxycarbonyl and ethoxycarbonyl. The bond to the parent moiety is through the carbonyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl, n-pentyl, heptyl, nonyl, decyl, fluoromethyl, trifluoromethyl and cyclopropylmethyl.

"Alkylaryl" means an alkyl-aryl- group in which the alkyl and aryl are as previously described. Preferred alkylaryls comprise a lower alkyl group. Non-limiting Examples of a suitable alkylaryl group is tolyl. The bond to the parent moiety is through the aryl.

"Alkylheteroaryl" means an alkyl-heteroaryl group in which the alkyl and heteroaryl groups are as previously described. The bond to the parent moiety is through the heteroaryl.

"Alkylsulfonyl" means an alkyl-S(O$_2$)— group in which the alkyl group is as previously described. Preferred groups are those in which the alkyl group is lower alkyl. The bond to the parent moiety is through the sulfonyl.

"Alkylthio" means an alkyl-S— group in which the alkyl group is as previously described. Non-limiting examples of suitable alkylthio groups include methylthio and ethylthio. The bond to the parent moiety is through the sulfur.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Aralkoxy" means an aralkyl-O— group in which the aralkyl group is as previously described. A non-limiting Example of a suitable aralkoxy is benzyloxy. The bond to the parent moiety is through the oxygen.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aralkoxycarbonyl" means an aralkyl-O—C(O)— group in which the aralkyl group is as previously described. Non-limiting Examples of a suitable aralkoxycarbonyl group is benzyloxycarbonyl. The bond to the parent moiety is through the carbonyl.

"Aralkylthio" means an aralkyl-S— group in which the aralkyl group is as previously described. Non-limiting Examples of a suitable aralkylthio group is benzylthio. The bond to the parent moiety is through the sulfur.

"Aroyl" means an aryl-C(O)— group in which the aryl group is as previously described. The bond to the parent moiety is through the carbonyl. Non-limiting examples of suitable groups include benzoyl and 1-naphthoyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(O)— group in which the aryl group is as previously described. Non-limiting examples of suitable aryloxycarbonyl groups include phenoxycarbonyl and naphthoxycarbonyl. The bond to the parent moiety is through the carbonyl.

"Arylsulfonyl" means an aryl-S($O_2$)— group in which the aryl group is as previously described. The bond to the parent moiety is through the sulfonyl.

"Arylthio" means an aryl-S— group in which the aryl group is as previously described. Non-limiting examples of suitable arylthio groups include phenylthio and naphthylthio. The bond to the parent moiety is through the sulfur.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylalkyl" means a cycloalkyl-alkyl- group in which the cycloalkyl and alkyl groups are as previously described.

"Cycloalkoxyalkyl" means a cycloalkyl-O-alkyl- group in which the cycloalkyl and alkyl groups are as previously described.

"Halo" means fluoro, chloro, bromo or iodo. Preferred are fluoro, chloro and bromo.

"Halogen" means fluorine, chlorine, bromine, or iodine. Preferred are fluorine, chlorine and bromine.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heteroaralkylthio" means a heteroaralkyl-S— group in which the heteroaralkyl is as previously described. Preferred heteroaralkylthios contain a lower alkyl group. The bond to the parent moiety is through the sulfur.

"Heteroaryl" means an aromatic monocyclic or multiclic ring system comprising about 5 to about 14 ring atoms, preferably about 5 to about 10 ring atoms, in which one or more of the ring atoms is an element other than carbon, for Examples nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom.

A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Heteroarylalkenyl" means a heteroaryl-alkenyl group in which the heteroaryl and the alkenyl are as previously described. Preferred heteroarylalkenyls contain a lower alkenyl group. The bond to the parent moiety is through the alkyl.

"Heteroarylalkynyl" means a heteroaryl-alkynyl group in which the heteroaryl and the alkynyl are as previously described. Preferred heteroarylalkynyls contain a lower alkynyl group. The bond to the parent moiety is through the alkynyl.

"Heteroarylsulfonyl" means a heteroaryl-S($O_2$)— group in which the heteroaryl group is as previously described. The bond to the parent moiety is through the sulfonyl.

"Heteroarylthio" means a heteroaryl-S— group in which the heteroaryl group is as previously described. The bond to the parent moiety is through the sulfur.

"Heterocyclyl" means a non-aromatic saturated monocyclic or multicyclic ring system comprising about 3 to about 10 ring atoms, preferably about 4 to about 7 ring atoms, in which one or more of the atoms in the ring system is an element other than carbon, for Examples nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(cbz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

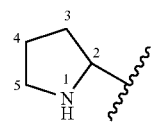

There is no —OH attached directly to carbons marked 2 and 5.

It should also be noted that tautomeric forms such as, for example, the moieties:

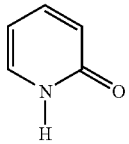 and 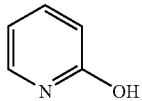

Are considered equivalent in certain embodiments of this invention.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and animals.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, keto, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NS(O$_2$)— and —S(O$_2$)NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

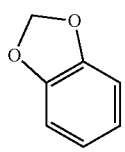 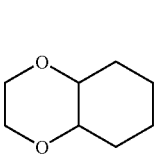 and 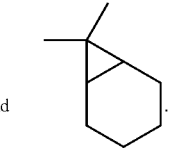.

The straight line ——— as a bond generally indicates a mixture of, or either of, the possible isomers, non-limiting example(s) include, containing (R)- and (S)-stereochemistry. For example,

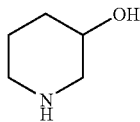 means containing both 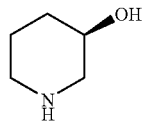

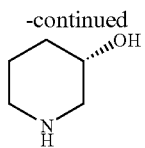

A dashed line (-----) represents an optional bond.

Lines drawn into the ring systems, such as, for example:

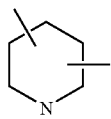 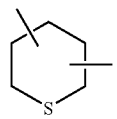 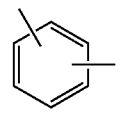

indicate that the indicated line (bond) may be attached to any of the substitutable ring atoms, non limiting examples of ring atoms include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

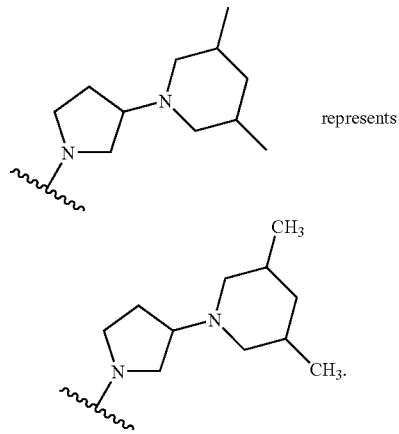

represents

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for Examples when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. Of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. Methyl, ethyl, and butyl chlorides, bromides and iodides), dialkyl sulfates (e.g. Dimethyl, diethyl, and dibutyl sulfates), long chain halides (e.g. Decyl, lauryl, and stearyl chlorides, bromides and iodides), aralkyl halides (e.g. Benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, esters, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect, for Example weight loss, diabetes control.

A preferred dosage is about 0.001 to 1000 mg/kg of body weight/day of the compound of Formula I or a pharmaceutically acceptable salt or solvate thereof. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula 1, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human):

A. An amount of a first compound, said first compound being a compound of Formula I, or a pharmaceutically acceptable salt or solvate of said compound; and B. An amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect (treating obesity).

Another aspect of this invention is a kit comprising:

A. An amount of a compound of Formula I, or a pharmaceutically acceptable salt or solvate of said compound and a pharmaceutically acceptable carrier, vehicle or diluent in a first unit dosage form;

B. An amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and C. Means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

Phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anoretic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human):

A. An amount of a first compound, said first compound being a compound of Formula I, or a pharmaceutically acceptable salt or solvate of said compound; and B. An amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising:

A first compound, said first compound being a compound of Formula I, or a pharmaceutically acceptable salt or solvate of said compound;

A second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally A pharmaceutical carrier, vehicle or diluent.

Another aspect of this invention is a kit comprising:

A. An amount of a compound of Formula I, or a pharmaceutically acceptable salt or solvate of said compound and a pharmaceutically acceptable carrier, vehicle or diluent in a first unit dosage form;

B. An amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and C. Means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As a Example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula 1 can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 mhz, $^1$H), Varian Gemini-300 (300 mhz) or XL-400 (400 mhz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:

Ar means an aryl group;
Bn means benzyl;
Boc means tert-Butoxycarbonyl;
BSA means bovine serum albumin
DBU means 1,8-diazabicyclo[5.4.0]undec-7-ene;
DCM means dichloromethane;
DIEA means Diisopropylethylamine
DMF means Dimethylformamide;
DPPA means diphenylphosphoryl azide;

ESI means electrospray ionization;
EtOAc means ethyl acetate;
HPLC means High Performance Liquid Chromatography;
Ki=Dissociation Constant for substrate/receptor complex;
Me means methyl or $CH_3$;
MS means mass spectrometry;
NEN means New England Nuclear, a commercial source for radio-labeled reagents;
NMR means nuclear magnetic resonance spectroscopy;
OTf means trifuoromethane sulfonate;
$Ph_3P$ means triphenyl phosphine;
Rf means retention factor;
Room temperature or rt (ambient) means about 25° C.;
SEM means 2-(trimethylsilyl)ethoxymethyl;
TBAF means tetrabutylammonium fluoride;
TBDPSCI means tert-butyldiphenylsilyl chloride;
TFA means trifluoroacetic acid
THF means tetrahydrofuran;
$Ti(OiPr)_4$ means titanium isopropoxide;
Alternative mechanistic pathways and analogous structures within the scope of the invention would be apparent to those skilled in the art.

EXPERIMENTAL EXAMPLES

The following schemes and preparative examples illustrate the preparation of some of the compounds of the invention and are not to be construed as limiting the scope of the invention disclosed herein.

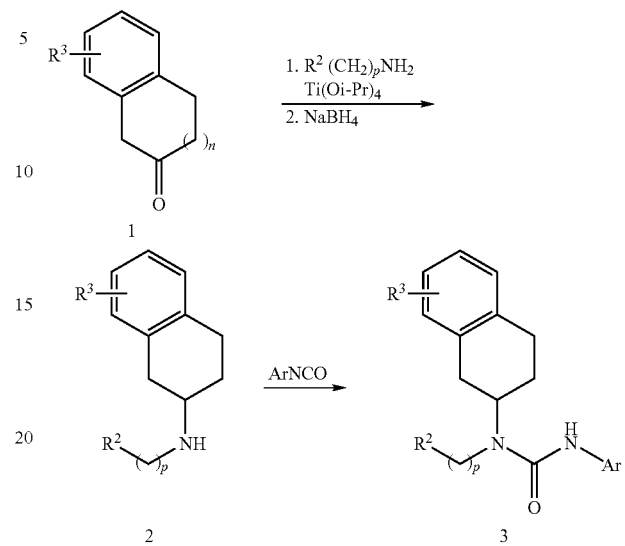

scheme 1, treatment of bicyclic ketone 1 with a primary amine and $Ti(Oi-Pr)_4$ followed by reaction with $NaBH_4$ provides secondary amine 2. Coupling of 2 with an isocyanate generates urea 3 of the invention.

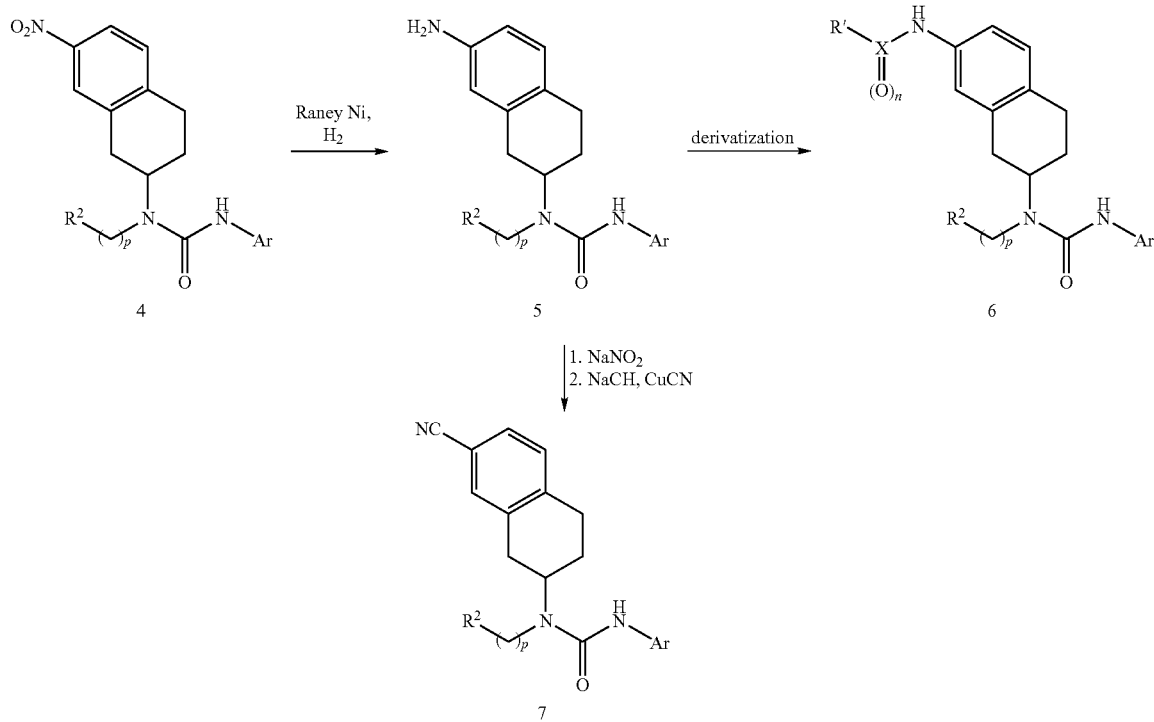

General Schemes

Schemes 1 to 4 illustrate the general synthetic pathways for the compounds of the invention.

In scheme 2, reduction of the nitro compound 4 using Raney Ni yields intermediate 5. Treatment of 5 with various derivatizing agents gives compound 6 of the invention. In addition, compound 5 can be converted to nitrile 7 via diazotization followed by reaction with NaCN and CuCN.

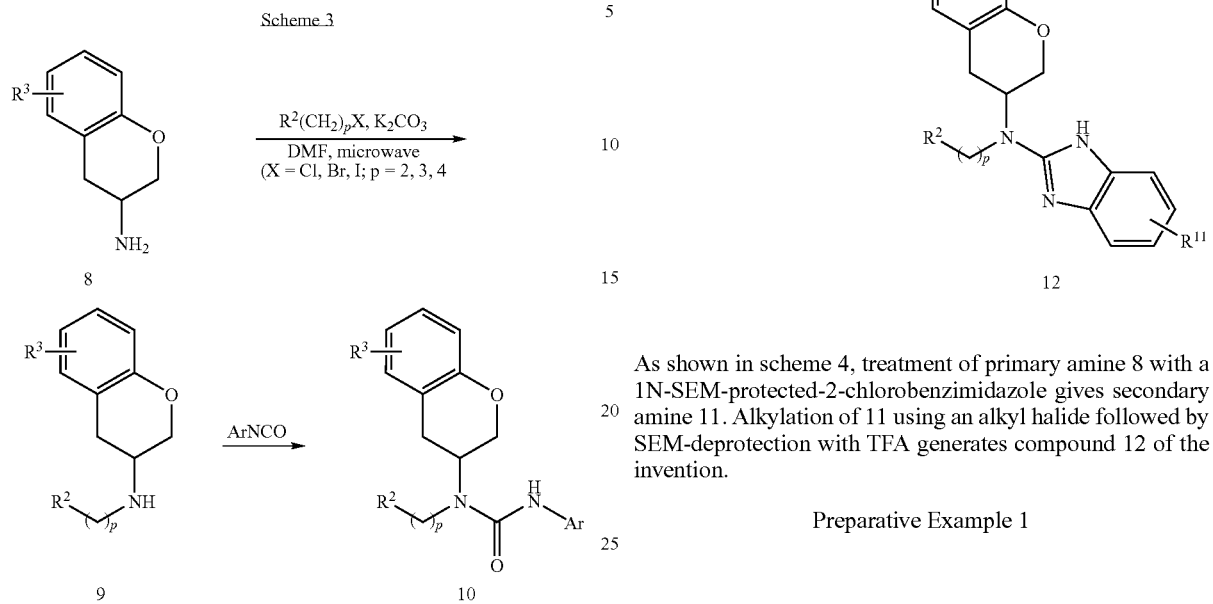

In scheme 3, treatment of primary amine 8 with an alkyl halide under microwave conditions gives secondary amine 9. Coupling of 9 with an isocyanate provides compound 10 of the invention.

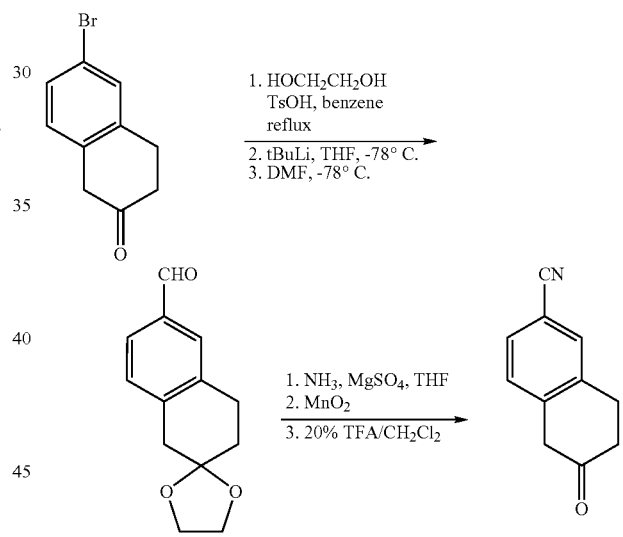

As shown in scheme 4, treatment of primary amine 8 with a 1N-SEM-protected-2-chlorobenzimidazole gives secondary amine 11. Alkylation of 11 using an alkyl halide followed by SEM-deprotection with TFA generates compound 12 of the invention.

Preparative Example 1

To a solution of 6-bromo-2-tetralone (5.36 g, 23.8 mmol) in benzene (5 mL) was added ethylene glycol (1.46 mL, 26.1 mmol, 1.1 eq) and p-toluenesulfonic acid (1.5 mg, catalyst). The mixture was heated at reflux and a Dean-Stark trap was used to collect the water produced. After 6 hours, TLC (25% EtOAc/hexanes) showed no 6-bromo-2-tetralone (Rf~0.5) left and a new spot (Rf~0.6) formed. The reaction mixture was cooled to room temperature, washed with 10% aqueous NaOH (2 mL) and $H_2O$ (5×2 mL), dried ($Na_2SO_4$), and concentrated in vacuo. The crude residue was chromatographed on silica gel by eluting with 10% EtOAc/hexanes to give 5.0 g (78%) of 6'-bromo-3',4'-dihydro-1'H-spiro[[1,3]dioxolane-2,2'-naphthalene] as a brown oil. $^1$H NMR (300 MHz, $CDCl_3$): δ 7.27 (s, 1H), 7.23 (d, 1H, J=8.1 Hz), 6.92 (d, 1H, J=8.1 Hz), 4.02 (s, 4H), 2.96 (t, 2H, J=6.9 Hz), 2.92 (s, 2H), 1.93 (t, 2H, J=6.9 Hz).

To a solution of 6'-bromo-3',4'-dihydro-1'H-spiro[[1,3]dioxolane-2,2'-naphthalene (1.53 g, 5.68 mmol) in anhydrous THF (12 mL) at −78° C. was added dropwise t-BuLi (1.7M in pentane, 7 mL, 11.9 mmol, 2.1 eq) over a period of 1 hour. After stirring for an additional 1.5 h at −78° C., a solution of DMF (0.95 mL, 12.2 mmol, 2.15 eq) in anhydrous THF (1.28 mL) was added dropwise over 20 min. The mixture was stirred for another 30 minutes at −78° C. TLC (25 EtOAc/hexanes) showed no starting material (Rf~0.6) left and a new spot (Rf~0.3) formed. The reaction mixture was warmed to room temperature and quenched with EtOAc (~10 mL) and saturated NH$_4$Cl (~10 mL). The organic layer was separated, dried (Na$_2$SO$_4$), and concentrated to give 0.84 g (68%) of crude 3',4'-dihydro-1'H-spiro[[1,3]dioxolane-2,2'-naphthalene]-6'-carbaldehyde as a colorless oil. $^1$H NMR (300 MHz, CDCl$_3$): δ 9.95 (s, 1H), 7.62 (m, 2H), 7.20 (d, 1H), 4.05 (s, 4H), 3.02 (m, 4H), 1.95 (t, 2H). The material was sufficiently pure and it was used in the next step without further purification.

Following the literature procedure of Lai, G. et al. (Synleft, 2001, 230-231), a stirred solution of 3',4'-dihydro-1'H-spiro[[1,3]dioxolane-2,2'-naphthalene]-6'-carbaldehyde (440 mg, 2.0 mmol) in THF (2 mL) was charged with NH$_3$ (2M solution in isopropanol, 15 mL, 30 mmol, 15 eq) and anhydrous MgSO$_4$ (3.64 g, 30 mmol, 15 eq). After 1 hour, MnO$_2$ (Aldrich, 85%, 3.1 g, 30 mmol, 15 eq) was added in small portions and the resulting mixture was stirred at room temperature for 20 hours. The reaction mixture was diluted with CH$_2$Cl$_2$ (40 mL) and filtered through Celite. The filtrate was concentrated in vacuo to give 0.42 g (100%) of 3',4'-dihydro-1'H-spiro[[1,3]dioxolane-2,2'-naphthalene]-6'-carbonitrile as a brown oil. $^1$H NMR (300 MHz, CDCl$_3$): δ 7.42 (s, 1H), 7.40 (d, 1H, J=8.0 Hz), 7.12 (d, 1H, J=8.0 Hz), 4.03 (s, 4H), 3.02 (s, 2H), 3.00 (t, 2H, J=6.9 Hz), 1.96 (t, 2H, J=6.9 Hz). The material was sufficiently pure and it was used in the next step without further purification.

A mixture of 3',4'-dihydro-1'H-spiro[[1,3]dioxolane-2,2'-naphthalene]-6'-carbonitrile (230 mg, 1.1 mmol), 20% TFA/CH$_2$Cl$_2$ (4 mL), and H$_2$O (~0.1 mL) was stirred at room temperature for 16 hours. TLC (50% EtOAc/hexanes) showed no starting material (Rf~0.95) left and a new spot (Rf~0.90) formed. The mixture was diluted with toluene (50 mL) and then concentrated in vacuo. The residue was diluted with toluene (50 mL) and concentrated again to give 0.23 g (100%) of 6-cyano-2-tetralone as an orange solid. $^1$H NMR (300 MHz, CDCl$_3$): δ 7.55 (s, 1H), 7.53 (d, 1H, J=7.8 Hz), 7.24 (d, 1H, J=7.8 Hz), 3.64 (s, 2H), 3.11 (t, 2H, J=6.6 Hz), 2.58 (t, 2H, J=6.6 Hz). As shown by the $^1$H NMR, the product was >95% pure, thus it was used without further purification.

Preparative Example 2

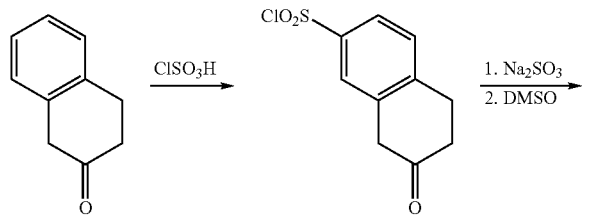

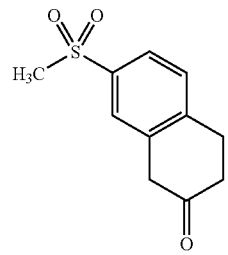

To chlorosulfonic acid (4.5 mL, 68 mmol), cooled to 0° C. in an ice-bath, was added 2-tetralone (1.8 mL, 14 mmol) dropwise over 45 min. After stirring at 0° C. for 2 hours, the mixture was poured slowly into crushed ice (~50 mL). After stirring for 1 hour, the mixture was extracted with EtOAc (2×50 mL). The combined EtOAc extracts were washed with H$_2$O (2×20 mL) and saturated brine (20 mL), dried (Na$_2$SO$_4$), and concentrated in vacuo to give 0.67 g (20%) of 7-oxo-5,6,7,8-tetrahydro-naphthalene-2-sulfonyl chloride as a yellow oil. $^1$H NMR (300 MHz, CDCl$_3$): δ 7.91 (d, 1H, J=8.1 Hz), 7.82 (s, 1H), 7.50 (d, 1H, J=8.1 Hz), 3.70 (s, 2H), 3.20 (t, 2H, J=6.6 Hz), 2.61 (t, 2H, J=6.6 Hz). The crude product was sufficiently pure and it was used in the next step without further purification.

Following the literature procedure of L. Field and R. D. Clark (Org. Syn., C.V. 4, 674), a mixture of Na$_2$SO$_3$ (1.19 g, 9.4 mmol) and NaHCO$_3$ (0.84 g, 10 mmol) in H$_2$O (4.8 mL) was heated at 75-80° C. for 10 min. The hot mixture was mixed with 7-methanesulfonly-3,4-dihydro-1H-naphthalen-2-one (1.24 g, 5.0 mmol) in a 100 mL round-bottom flask. After heating at 75-80° C. for 1.5 hours, the mixture was cooled to room temperature and then left stand at room temperature for 16 hours. NaHCO$_3$ (0.42 g, 5.0 mmol) and Me$_2$SO$_4$ (2.4 mL, 25 mmol) were added and the mixture was heated at reflux for 1.5 hours. After cooling to room temperature, the mixture was diluted with EtOAc (20 mL) and the organic layer was separated. The aqueous layer was extracted with EtOAc (3×20 mL) and the combined organic layer was dried (Na$_2$SO$_4$) and concentrated in vacuo. Chromatography on silica using 50% EtOAc/hexanes gave 0.23 g (20%) of 7-oxo-5,6,7,8-tetrahydro-naphthalene-2-sulfonyl chloride as a yellow solid. $^1$H NMR (300 MHz, CDCl$_3$): δ 7.80 (d, 1H, J=8.1 Hz), 7.12 (s, 1H), 7.45 (d, 1H, J=8.1 Hz), 3.67 (s, 2H), 3.16 (t, 2H, J=6.9 Hz), 3.05 (s, 3H), 2.58 (t, 2H, J=6.9 Hz).

Preparative Example 3

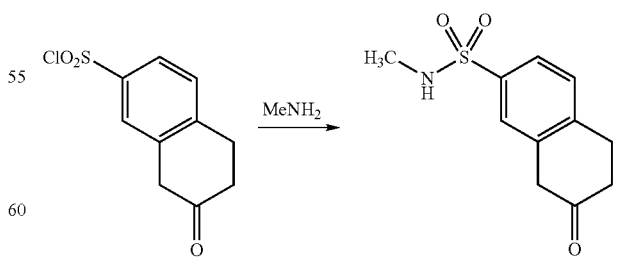

To a solution of 7-oxo-5,6,7,8-tetrahydro-naphthalene-2-sulfonyl chloride (see Preparative Example 3, 1.14 g, 4.7 mmol) in CH$_2$Cl$_2$ (10 mL) at 15° C. (using a water bath) was added MeNH$_2$ (2M in THF, 7 mL, 14 mmol, 3 eq) dropwise.

After stirring at room temperature for 30 minutes, the mixture was diluted with CH$_2$Cl$_2$ (30 mL), washed with H$_2$O (20 mL), dried (Na$_2$SO$_4$), and concentrated. The residue was chromatographed on silica by eluting with 20% EtOAc/hexanes to give 0.45 g (40%) of 7-oxo-5,6,7,8-tetrahydro-naphthalene-2-sulfonic acid methylamide as a yellow oil. $^1$H NMR (300 MHz, CDCl$_3$): δ 7.70 (d, 1H, J=8.1 Hz), 7.63 (s, 1H), 7.40 (d, 1H, J=8.1 Hz), 4.66 (q, 1H, J=5.4 Hz), 3.64 (s, 2H), 3.14 (t, 2H, J=6.6 Hz), 3.65 (d, 3H, J=5.4 Hz), 2.57 (t, 2H, J=6.6 Hz).

Preparative Example 4

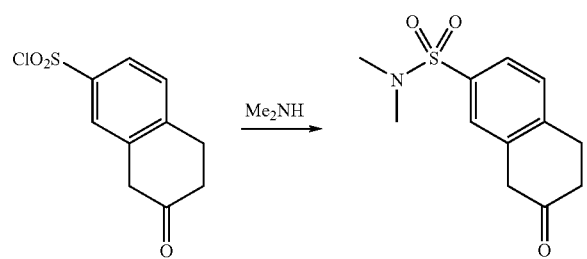

To a solution of 7-oxo-5,6,7,8-tetrahydro-naphthalene-2-sulfonyl chloride (see Preparative Example 3, 1.0 g, 4.1 mmol) in CH$_2$Cl$_2$ (10 mL) at 15° C. (using a water bath) was added Me$_2$NH (2M in THF, 8 mL, 16 mmol, 4 eq) dropwise. After stirring at room temperature for 30 minutes, the mixture was diluted with CH$_2$Cl$_2$ (30 mL), washed with H$_2$O (20 mL), dried (Na$_2$SO$_4$), and concentrated. The residue was chromatographed on silica using 20% EtOAc/hexanes to give 0.46 g (45%) of 7-oxo-5,6,7,8-tetrahydro-naphthalene-2-sulfonic acid dimethylamide as a yellow oil. $^1$H NMR (300 MHz, CDCl$_3$): δ 7.61 (d, 1H, J=8.1 Hz), 7.53 (s, 1H), 7.41 (d, 1H, J=8.1 Hz), 3.65 (s, 2H), 3.14 (t, 2H, J=6.6 Hz), 2.71 (s, 6H), 2.58 (t, 2H, J=6.6 Hz).

Preparative Example 5

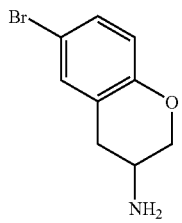

6-Bromo-chroman-3-ylamine was prepared according to the literature procedure described by Andersson, B. R. et al. WO9012795. Thus, a mixture of 5-bromosalicylaldehyde (9.5 g, 47 mmol), di-n-butylammonium chloride (3.8 g, 23 mmol), and 2-nitroethanol (6.8 g, 75 mmol) in amyl acetate (60 mL) was heated at reflux for 3 hours with a Dean-Stark apparatus under nitrogen atmosphere. The solvent was removed in vacuo and the product was dissolved in CH$_2$Cl$_2$ (280 mL) followed by the addition of NaCNBH$_3$ (9.6 g, 150 mmol). The mixture was stirred for 30 minutes and water (100 mL) was added to quench the reaction. The organic layer was separated and the aqueous layer was extracted with CH$_2$Cl$_2$ (50 mL×3). The combined organic layers were washed with brine, dried (Na$_2$SO$_4$), and concentrated in vacuo. The crude product was chromatographed on silica gel by eluting with 1:1 hexane/CH$_2$Cl$_2$ to give 4.4 g (40%) of pure 6-bromo-3-nitro-chroman as a light yellow solid. $^1$H NMR (300 MHz, CDCl$_3$): δ 7.18 (m, 2H), 6.68 (d, J=8.4 Hz, 1H), 4.88 (m, 1H), 4.62 (m, 1H), 4.32 (m, 1H), 4.47 (m, 1H), 3.28 (dd, J=17.4, 6.0 Hz, 1H).

To a solution of 6-bromo-3-nitro-chroman (2.18 g, 8.4 mmol) in glacial acetic acid (150 mL) was added zinc dust (11 g, 170 mmol). The mixture was heated to 100° C. for 20 min. The zinc dust was filtered off and washed with CH$_2$Cl$_2$. The solvent was evaporated in vacuo and the residue partitioned between 1N aqueous HCl (40 mL) and CH$_2$Cl$_2$ (40 mL). The aqueous phase was separated and its pH was adjusted to 11 with 2N NaOH, which was then extracted with CH$_2$Cl$_2$ (50 mL×3). The combined organic phase was dried (Na$_2$SO$_4$) and concentrated in vacuo to give 1.2 g (63%) of 6-bromo-chroman-3-ylamine as a brown solid. $^1$H NMR (300 MHz, CDCl$_3$): δ 7.13 (m, 2H), 6.63 (d, J=7.8Hz, 1H), 4.05 (d, J=10.2Hz, 1H), 3.74 (dd, J=1.5, 6.6 Hz, 1H), 3.31 (br.s, 1H), 2.94 (dd, J=16.2, 6.9 Hz, 1H), 1.35 (br.s, 2H).

Preparative Example 6

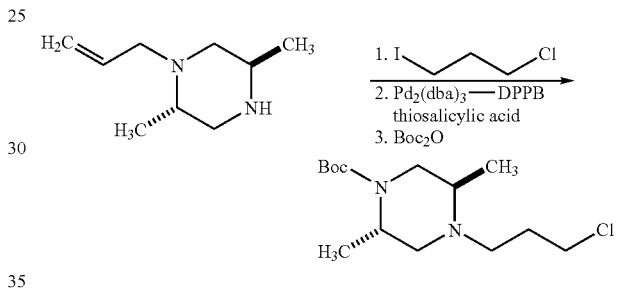

A mixture of (+)-(2S,5R)-1-allyl-2,5-dimethylpiperazine (10.6 g, 68.7 mmol, prepared according to the literature procedure described by Janetka, J. W. et al., J. Org. Chem., 2003, 68, 3976-3980), 1-chloro-3-iodo-propane (16.9 g, 82.8 mmol, 1.2 eq), and K$_2$CO$_3$ (24.6 g, 178 mmol, 2.6 eq) in acetone (230 mL) was heated at 50° C. for 16 hours. The mixture was cooled to room temperature, filtered through Celite, and the filtrate was concentrated in vacuo. Chromatography on silica gel using a gradient of 2M NH$_3$/MeOH in CH$_2$Cl$_2$ (0-2%) gave 14.05 g (89%) of (2S,5R)-1-allyl-4-(3-chloro-propyl)-2,5-dimethyl-piperazine as a light yellow oil.

To a solution of (2S,5R)-1-allyl-4-(3-chloro-propyl)-2,5-dimethyl-piperazine (14.05 g, 61 mmol) in anhydrous THF (78 mL) under argon was added thiosalicylic acid (10.33 g, 67 mmol, 1.1 eq) followed by the addition of a solution of tris(dibenzylidenacetone)-dipalladium (Pd$_2$(dba)$_3$, 2.8 g, 3.1 mmol, 5 mol %) and 1,4-bis(diphenylphosphino)butane (DPPB, 1.33 g, 3.1 mmol, 5 mol %) in anhydrous THF (26 mL, pre-mixed for 15 minutes). After stirring at room temperature for 2 hours, the mixture was filtered through Celite. The filtrate was concentrated in vacuo and the residue was partitioned between 1N aqueous HCl (70 mL) and Et$_2$O (70 mL). The aqueous layer was separated and extracted with Et$_2$O (50 mL×2), and treated with NaOH (solid) to bring its pH to 13. The aqueous phase was extracted with CHCl$_3$ (50 mL×4). The combined organic phase was dried (Na$_2$SO$_4$) and concentrated in vacuo to give 11.6 g (100%) of (2S,5R)-4-(3-chloro-propyl)-2,5-dimethyl-piperazine as a light yellow oil.

To a solution of (2S,5R)-4-(3-chloro-propyl)-2,5-dimethyl-piperazine (11.6 g, 61 mmol) in CH$_2$Cl$_2$ (240 mL) at 0° C. was added Boc$_2$O (14.9 g, 67 mmol, 1.1 eq) and the mixture was stirred at room temperature for 16 hours. The solvent was evaporated and the residue was chromatographed on silica gel by eluting with 30% EtOAc/hexane to give 12.8 g (72%) of (2S,5R)-4-(3-chloro-propyl)-2,5-dimethyl-piperazine-1-carboxylic acid tert-butyl ester as a light yellow oil. $^1$H NMR (300 MHz, CDCl$_3$): δ 4.22 (m, 1H), 3.64 (m, 3H), 3.23 (dd, J=11.4, 3.9 Hz, 1H), 2.55 (m, 1H), 2.42 (m, 1H), 2.22 (d, J=11.4 Hz, 1H), 1.87 (t, J=6.3 Hz, 2H), 1.46 (s, 9H), 1.21 (d, J=6.9 Hz, 3H), 0.92 (d, J=6.6 Hz, 3H).

Preparative Example 7

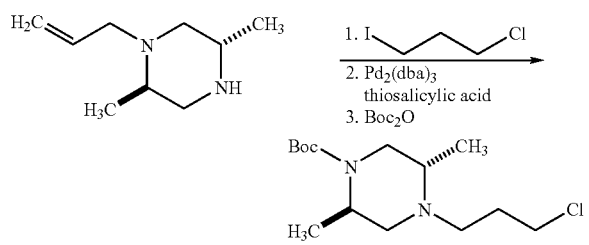

Following the same procedure used in Preparative Example 6, (−)-(2R,5S)-1-allyl-2,5-dimethylpiperazine (prepared according to the literature procedure by Janetka, J. W. et al., J. Org. Chem., 2003, 68, 3976-3980) was converted to (2R,5S)-4-(3-chloro-propyl)-2,5-dimethyl-piperazine-1-carboxylic acid tert-butyl ester as a light yellow oil. $^1$H NMR (300 MHz, CDCl$_3$): δ 4.22 (m, 1H), 3.64 (m, 3H), 3.23 (dd, J=11.4, 3.9 Hz, 1H), 2.55 (m, 1H), 2.42 (m, 1H), 2.22 (d, J=11.4 Hz, 1H), 1.87 (t, J=6.3 Hz, 2H), 1.46 (s, 9H), 1.21 (d, J=6.9 Hz, 3H), 0.92 (d, J=6.6 Hz, 3H).

Preparative Example 8

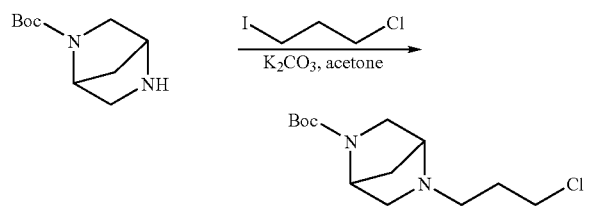

To a solution of 2,5-diaza-bicyclo[2.2.1]heptane-2-carboxylic acid tert-butyl ester (0.10 g, 0.50 mmol) in acetone (2 mL) was added 1-chloro-3-iodo-propane (0.10 g, 0.50 mmol, 1 eq) and K$_2$CO$_3$ (0.084 g, 0.60 mmol, 1.2 eq). The mixture was heated at 50° C. for 3 h and then cooled to r.t. The mixture was filtered through Celite and the filtrate was concentrated in vacuo. Chromatography on silica gel by eluting with 5% MeOH/CH$_2$Cl$_2$ gave 0.095 g (69%) of 5-(3-chloro-propyl)-2,5-diaza-bicyclo[2.2.1]heptane-2-carboxylic acid tert-butyl ester as a yellowish oil. $^1$H NMR (300 MHz, CDCl$_3$): δ 4.20 (m, 1H), 3.58 (m, 2H), 3.46 (m, 2H), 3.12 (m, 1H), 2.86 (m, 1H), 2.62 (m, 3H), 1.82 (m, 3H), 1.66 (m, 1H), 1.41 (s, 9H).

By analogy to Preparative Example 8, substituted and/or unsubstituted 1-(3-chloro-propyl)-pyrrolidine and 1-(3-chloro-propyl)-piperidine groups can be prepared with pyrrolidine and piperidine respectively.

Preparative Example 9

Compound XVII from Table 1

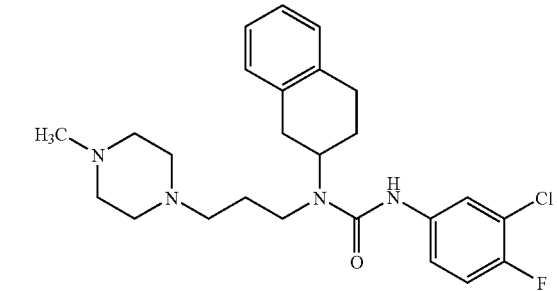

A neat mixture of 2-tetralone (0.552 g, 3.78 mmol), 1-(3-aminopropyl)-4-methylpiperazine (0.713 g, 4.54 mmol, 1.2 eq), and titanium (IV) isopropoxide (1.44 g, 5.67 mmol, 1.5 eq) was heated at 80° C. for 3 hours. The mixture was cooled to 0° C., diluted with 5 mL of MeOH, and then treated with NaBH$_4$ (0.143 g, 3.78 mmol, 1 eq, adding portionwise). The resulting mixture was stirred at 0° C. for 30 min and then at room temperature for 12 hours. The reaction mixture was concentrated in vacuo, treated with water (3 mL) and then MeOH (30 mL), filtered through Celite. The filtrate was concentrated in vacuo, and the residue was redissolved in water (25 mL) and extracted with CHCl$_3$ (3×25 mL). The combined CHCl$_3$ extracts were dried (MgSO$_4$) and concentrated to give [3-(4-methyl-piperazin-1-yl)-propyl]-(1,2,3,4-tetrahydro-naphthalen-2-yl)-amine as a dark brown oil (0.721 g, 67%). The crude intermediate was used in the subsequent step without further purification.

To a solution of [3-(4-methyl-piperazin-1-yl)-propyl]-(1,2,3,4-tetrahydro-naphthalen-2-yl)-amine (0.144 g, 0.50 mmol) in CH$_2$Cl$_2$ (1 mL) was added 3-chcloro-4-fluoro-phenylisocyante (0.086 g, 0.50 mmol, 1 eq). The mixture was stirred at room temperature for 16 hours. Isocyanate resin (NovaBiochem 1.3 mmol/g loading, 0.358 g, 0.5 mmol) was added and the mixture was agitated for 3 hours. The mixture was filtered and the resin was washed with CH$_2$Cl$_2$ (5×1 mL). The combined filtrate was concentrated and the residue was purified on reverse-phase HPLC to give 0.110 g (48%) of 3-(3-chloro-4-fluoro-phenyl)-1-[3-(4-methyl-piperazin-1-yl)-propyl]-1-(1,2,3,4-tetrahydro-naphthalen-2-yl)-urea as a white solid. $^1$H NMR (300 MHz, CD$_3$OD): δ 7.52 (dd, 1H), 7.21 (m, 1H), 7.08 (d, 1H), 7.02 (s, 4H), 4.25 (m, 1H), 3.60-3.35 (m, 10H), 3.10 (t, 2H), 2.90 (m, 4H), 2.85 (s, 3H), 1.98 (m, 4H). MS-ESI: 459.2 (M+H$^+$).

In this and the following Preparative Examples, commercially available 3-pyrrolidin-1-yl-propylamine and 3-piperidin-1-yl-propylamine groups can be used analogously to the 3-piperazin-1-yl-propylamine groups.

Preparative Example 10

Compound XIX from Table 1

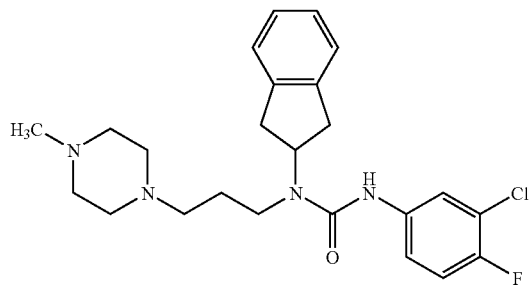

Following a similar procedure as in Preparative Example 9 except replacing 2-tetralone with 2-indanone, 0.013 g of 3-(3-chloro-4-fluoro-phenyl)-1-indan-2-yl-1-[3-(4-methyl-piperazin-1-yl)-propyl]-urea was obtained as a colorless gum. 1H NMR (300 MHz, CD$_3$OD): δ 7.70 (dd, 1H), 7.39 (m, 3H), 7.30 (m, 3H), 5.00 (m, 1H), 3.65-3.35 (m, 10H), 3.25-3.05 (m, 4H), 3.01 (s, 3H), 2.05 (m, 2H). MS-ESI: 445.1 (M+H$^+$).

Preparative Example 11

Compound X from Table 1

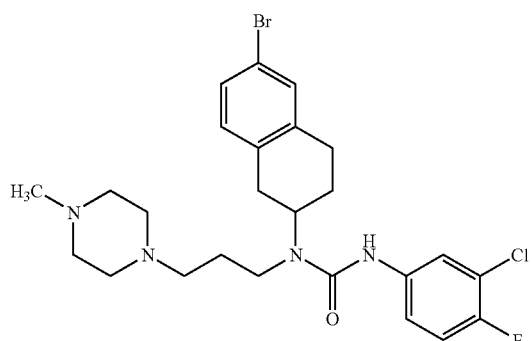

Following a similar procedure as in Preparative Example 9 except replacing 2-tetralone with 6-bromo-2-tetralone, 0.033 g of 1-(6-bromo-1,2,3,4-tetrahydro-naphthalen-2-yl)-3-(3-chloro-4-fluoro-phenyl)-1-[3-(4-m ethyl-piperazin-1-yl)-propyl]-urea was obtained as a white solid. $^1$H NMR (300 MHz, CD$_3$OD): δ 7.70 (dd, 1H), 7.40 (m, 3H), 7.25 (t, 1H), 7.15 (d, 1H), 4.40 (m, 1H), 3.70-3.50 (m, 10H), 3.30 (t, 2H), 3.10 (m, 4H), 3.01 (s, 3H), 2.18 (m, 4H). MS-ESI: 537.1 (M+H$^+$).

Preparative Example 12

Compound XII from Table 1

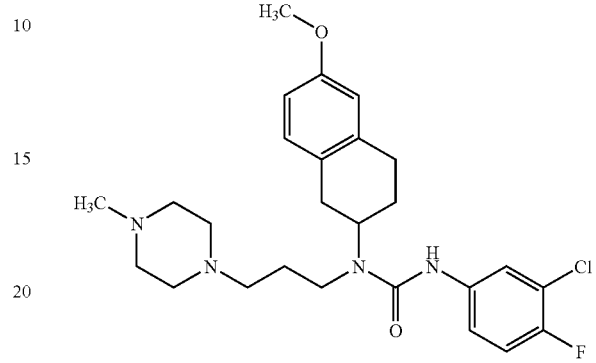

Following a similar procedure as in Preparative Example 9 except replacing 2-tetralone with 6-bromo-2-tetralone, 0.120 g of 3-(3-chloro-4-fluoro-phenyl)-1-(6-methoxy-1,2,3,4-tetrahydro-naphthalen-2-yl)-1-[3-(4-methyl-piperazin-1-yl)-propyl]-urea was obtained as a white solid. $^1$H NMR (300 MHz, CD$_3$OD): δ 7.70 (dd, 1H), 7.40 (m, 1H), 7.22 (t, 1H), 7.13 (d, 1H), 6.80 (m, 2H), 4.39 (m, 1H), 3.85 (s, 3H), 3.70 (m, 8H), 3.58 (m, 2H), 3.33 (t, 2H), 3.10 (m, 7H), 2.17 (m, 4H). MS-ESI: 489.2 (M+H$^+$).

Preparative Example 13

Compound VII from Table 1

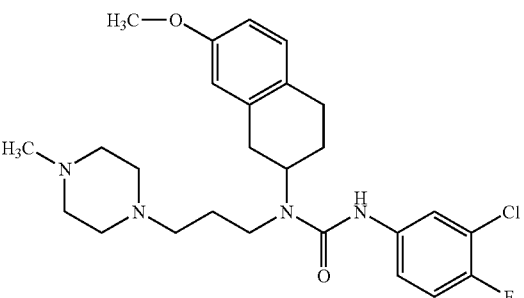

Following a similar procedure as in Preparative Example 9 except replacing 2-tetralone with 7-methoxy-2-tetralone, 0.114 g of 3-(3-chloro-4-fluoro-phenyl)-1-(7-methoxy-1,2,3,4-tetrahydro-naphthalen-2-yl)-1-[3-(4-methyl-piperazin-1-yl)-propyl]-urea was obtained as a white solid. $^1$H NMR (300 MHz, CDCl$_3$): δ 9.21 (s, 1H), 7.52 (dd, 1H), 7.37 (m, 1H), 7.05 (t, 1H), 6.98 (d, 1H), 6.68 (dd, 1H), 6.59 (d, 1H), 4.32 (m, 1H), 3.75 (s, 3H), 3.37 (t, 2H), 3.05 (t, 1H), 2.85 (m, 3H), 2.60-2.30 (m, 10H), 2.25 (s, 3H), 2.00 (m, 2H, 1.80 (m, 2H). MS-ESI: 489.1 (M+H$^+$).

Preparative Example 14

Compound XXVIII from Table 1

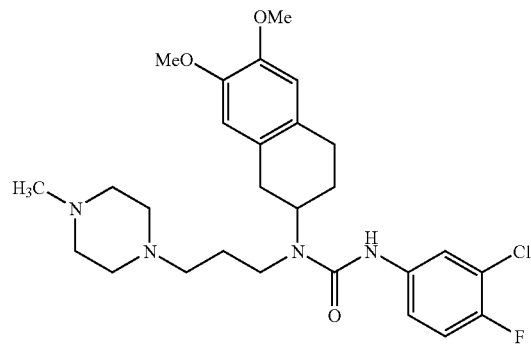

Following a similar procedure as in Preparative Example 9 except replacing 2-tetralone with 6,7-dimethoxy-2-tetralone, 0.045 g of 3-(3-chloro-4-fluoro-phenyl)-1-(6,7-dimethoxy-1,2,3,4-tetrahydro-naphthalen-2-yl)-1-[3-(4-methyl-piperazin-1-yl)-propyl]-urea was obtained as a white solid. $^1$H NMR (300 MHz, CDCl$_3$): δ 9.20 (s, 1H), 7.52 (dd, 1H, J=6.6, 2.7 Hz), 7.35 (m, 1H), 7.04 (t, 1H, J=9.0 Hz), 6.56 (s, 1H), 6.52 (s, 1H), 4.32 (m, 1H), 3.82 (s, 3H), 3.80 (s, 3H), 3.38 (t, 2H, J=6.0 Hz), 3.05-2.75 (m, 4H), 2.60-2.30 (m, 10H), 2.25 (s, 3H), 2.00 (m, 2H), 1.80 (m, 2H). MS-ESI: 519.0 (M+H$^+$).

Preparative Example 15

Compound XX from Table 1

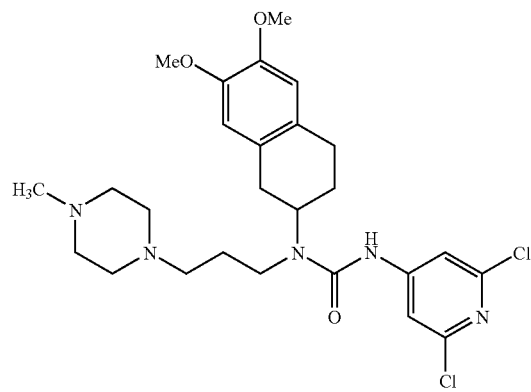

Following a similar procedure as in Preparative Example 9 except replacing 2-tetralone with 6,7-dimethoxy-2-tetralone and replacing 3-chcloro-4-fluoro-phenylisocyante with 2,6-dichloro-4-isocyanato-pyridine, 0.036 g of 3-(2,6-dichloro-pyridin-4-yl)-1-(6,7-dimethoxy-1,2,3,4-tetrahydro-naphthalen-2-yl)-1-[3-(4-methyl-piperazin-1-yl)-propyl]-urea was obtained as a white solid. $^1$H NMR (300 MHz, CDCl$_3$): δ 9.72 (s, 1H), 7.59 (s, 2H), 6.59 (s, 1H), 6.52 (s, 1H), 4.20 (m, 1H), 3.83 (s, 3H), 3.81 (s, 3H), 3.40 (t, 2H, J=6.0 Hz), 3.20 (t, 1H), 2.85 (m, 3H), 2.65-2.45 (m, 10H), 2.38 (s, 3H), 1.85 (m, 2H), 1.62 (m, 2H). MS-ESI: 536.0 (M+H$^+$).

Preparative Example 16

Compound XVI from Table 1

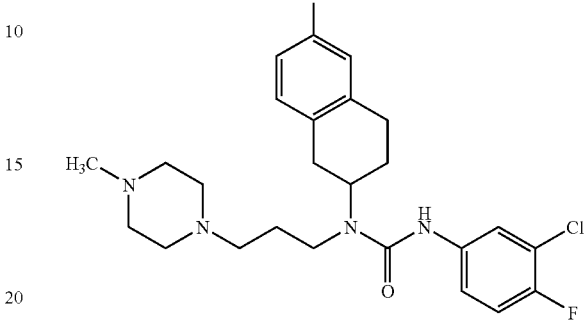

Following a similar procedure as in Preparative Example 9 except replacing 2-tetralone with 6-cyano-2-tetralone, 0.048 g of 3-(3-chloro-4-fluoro-phenyl)-1-(6-cyano-1,2,3,4-tetrahydro-naphthalen-2-yl)-1-[3-(4-me thyl-piperazin-1-yl)-propyl]-urea was obtained as a white solid. $^1$H NMR (300 MHz, CD$_3$OD): δ 7.60 (dd, 1H, J=6.6, 2.7 Hz), 7.51 (s, 1H), 7.47 (dd, 1H, J=7.8, 1.8 Hz), 7.30 (m, 2H), 7.16 (t, 1H, J=9.0 Hz), 4.32 (m, 1H), 3.55-3.35 (m, 10H), 3.15-3.00 (m, 6H), 2.93 (s, 3H), 2.08 (m, 4H). MS-ESI: 484.1 (M+H$^+$).

Preparative Example 17

Compound VI from Table 1

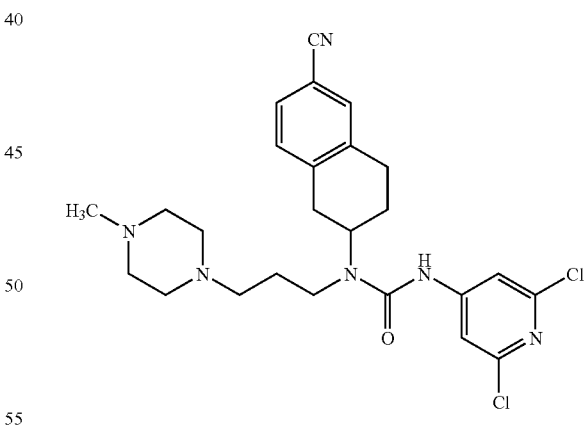

Following a similar procedure as in Preparative Example 9 except replacing 2-tetralone with 6-cyano-2-tetralone and replacing 3-chcloro-4-fluoro-phenylisocyanate with 2,6-dichloro-4-isocyanato-pyridine, 0.037 g of 3-(2,6-dichloro-pyridin-4-yl)-1-(6-cyano-1,2,3,4-tetrahydro-naphthalen-2-yl)-1-[3-(4-m ethyl-piperazin-1-yl)-propyl]-urea was obtained as a white solid. $^1$H NMR (300 MHz, CD$_3$OD): δ 7.59 (s, 2H), 7.51 (s, 1H), 7.46 (d, 1H, J=8.1 Hz), 7.29 (d, 1H, J=8.1 Hz), 4.33 (m, 1H), 3.60-3.35 (m, 10H), 3.20-3.00 (m, 6H), 2.95 (s, 3H), 2.08 (m, 4H). MS-ESI: 501.0 (M+H$^+$).

Preparative Example 18

Compound XIV from Table 1

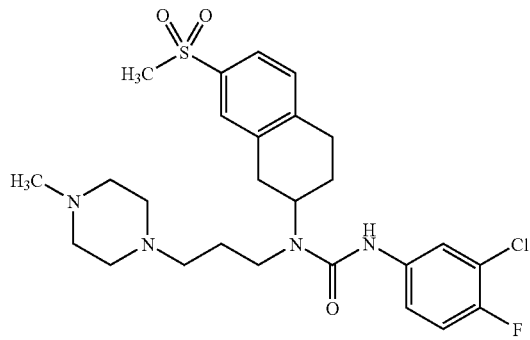

Following a similar procedure as in Preparative Example 9 except replacing 2-tetralone with 7-methanesulfonyl-2-tetralone, 0.044 g of 3-(3-chloro-4-fluoro-phenyl)-1-(7-methanesulfonyl-1,2,3,4-tetrahydro-naphthalen-2-yl)-1-[3-(4-methyl-piperazin-1-yl)-propyl]-urea was obtained as a white solid. $^1$H NMR (300 MHz, CDCl$_3$): δ 9.08 (s, 1H), 7.66 (d, 1H), 7.63 (s, 1H), 7.52 (dd, 1H, J=6.6, 1.8 Hz), 7.35 (m, 1H), 7.28 (d, 1H), 7.07 (t, 1H, J=8.7 Hz), 4.28 (m, 1H), 3.40 (t, 2H, J=6.0 Hz), 3.18 (m, 1H), 3.02 (m, 7H), 2.65-2.45 (m, 6H), 2.33 (s, 3H), 2.08 (m, 2H), 1.84 (m, 2H). MS-ESI: 537.1 (M+H$^+$).

Preparative Example 19

Compound XIII from Table 1

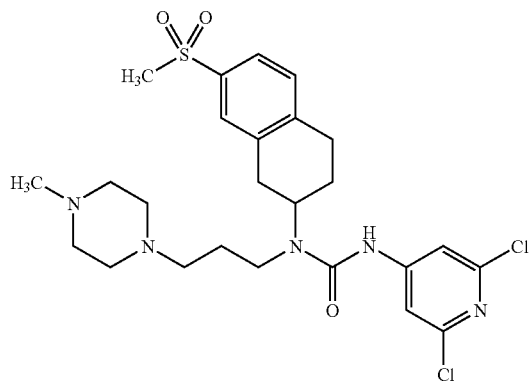

Following a similar procedure as in Preparative Example 9 except replacing 2-tetralone with 7-methanesulfonyl-2-tetralone and replacing 3-chcloro-4-fluoro-phenylisocyanate with 2,6-dichloro-4-isocyanato-pyridine, 0.020 g of 3-(2,6-dichloro-pyridin-4-yl)-1-(7-methanesulfonyl-1,2,3,4-tetrahydro-naphthalen-2-yl)-1-[3-(4-methyl-piperazin-1-yl)-propyl]-urea was obtained as a white solid. $^1$H NMR (300 MHz, CD$_3$OD): δ 7.70 (m, 2H), 7.59 (s, 2H), 7.40 (d, 1H, J=8.1 Hz), 4.36 (m, 1H), 3.50-3.45 (m, 6H), 3.25 (m, 2H), 3.20-3.05 (m, 6H), 2.98 (t, 2H, J=7.5 Hz), 2.91 (s, 3H), 2.12 (m, 2H), 2.02 (m, 2H). MS-ESI: 554.0 (M+H$^+$).

Preparative Example 20

Compound XXIX from Table 1

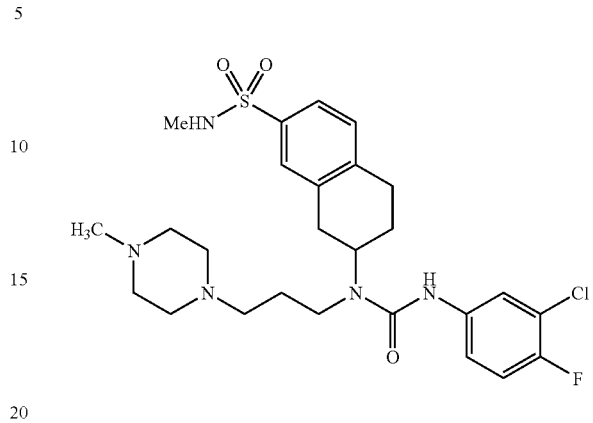

Following a similar procedure as in Preparative Example 9 except replacing 2-tetralone with 7-oxo-5,6,7,8-tetrahydro-naphthalene-2-sulfonic acid methylamide, 0.045 g of 7-{3-(3-chloro-4-fluoro-phenyl)-1-[3-(4-methyl-piperazin-1-yl)-propyl]-ureido}-5,6,7,8-tetrahydro-naphthalene-2-sulfonic acid methylamide was obtained as a white solid. $^1$H NMR (300 MHz, CDCl$_3$): δ 9.32 (s, 1H), 7.52 (m, 3H), 7.33 (m, 1H), 7.20 (d, 1H, J=8.7 Hz), 7.05 (t, 1H, J=8.7 Hz), 4.66 (m, 1H), 4.27 (m, 1H), 3.38 (t, 2H, J=5.7 Hz), 3.14 (m, 1H), 2.98 (m, 3H), 2.59 (d, 3H, J=4.5 Hz), 2.55-2.30 (m, 10H), 2.25 (s, 3H), 2.05 (m, 2H), 1.81 (m, 2H). MS-ESI: 552.3 (M+H$^+$).

Preparative Example 21

Compound XXVII from Table 1

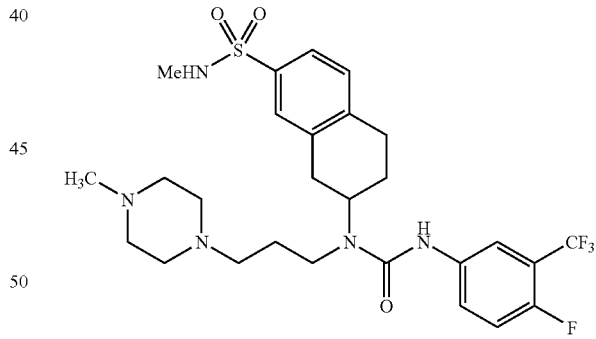

Following a similar procedure as in Preparative Example 9 except replacing 2-tetralone with 7-oxo-5,6,7,8-tetrahydro-naphthalene-2-sulfonic acid methylamide and replacing 3-chcloro-4-fluoro-phenylisocyanate with 3-trifluoromethyl-4-fluoro-phenylisocyanate, 0.040 g of 7-{3-(4-fluoro-3-trifluoromethyl-phenyl)-1-[3-(4-methyl-piperazin-1-yl)-propyl]-ureido}-5,6,7,8-tetrahydro-naphthalene-2-sulfonic acid methylamide was obtained as a white solid. $^1$H NMR (300 MHz, CDCl$_3$): δ 9.48 (s, 1H), 7.74 (m, 1H), 7.61-7.50 (m, 3H), 7.22 (d, 1H, J=8.1 Hz), 7.14 (t, 1H, J=9.3 Hz), 4.34 (m, 1H), 4.28 (m, 1H), 3.41 (t, 2H, J=5.7 Hz), 3.17 (m, 1H), 3.00 (m, 3H), 2.63 (d, 3H, J=5.1 Hz), 2.60-2.30 (m, 10H), 2.24 (s, 3H), 2.08 (m, 2H), 1.83 (m, 2H). MS-ESI: 586.0 (M+H$^+$).

Preparative Example 22

Compound XXII from Table 1

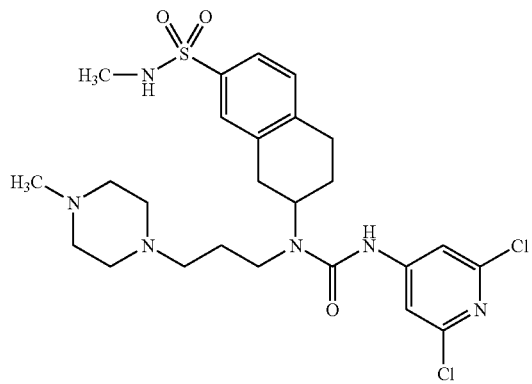

Following a similar procedure as in Preparative Example 9 except replacing 2-tetralone with 7-oxo-5,6,7,8-tetrahydro-naphthalene-2-sulfonic acid methylamide and replacing 3-chcloro-4-fluoro-phenylisocyante with 2,6-dichloro-4-isocyanato-pyridine, 0.050 g of 7-{3-(2,6-dichloro-pyridin-4-yl)-1-[3-(4-methyl-piperazin-1-yl)-propyl]-ureido}-5,6,7,8-tetrahydro-naphthalene-2-sulfonic acid methylamide was obtained as a white solid. $^1$H NMR (300 MHz, CD$_3$OD): δ 7.60-7.54 (m, 4H), 7.33 (d, 1H), 4.30 (m, 1H), 3.45 (t, 2H), 3.20 (m, 1H), 3.20-2.90 (m, 3H), 2.60-2.40 (m, 13H), 2.31 (s, 3H), 2.09 (m, 2H), 1.88 (m, 2H). MS-ESI: 569.0 (M+H$^+$).

Preparative Example 23

Compound XXX from Table 1

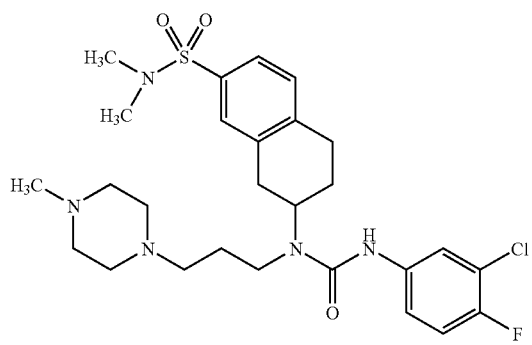

Following a similar procedure as in Preparative Example 9 except replacing 2-tetralone with 7-oxo-5,6,7,8-tetrahydro-naphthalene-2-sulfonic acid dimethylamide, 0.036 g of 7-{3-(3-chloro-4-fluoro-phenyl)-1-[3-(4-methyl-piperazin-1-yl).-propyl]-ureido}-5,6,7,8-tetrahydro-naphthalene-2-sulfonic acid dimethylamide was obtained as a white solid. $^1$H NMR (300 MHz, CDCl$_3$): δ 9.32 (s, 1H), 7.52 (dd, 1H, J=6.6, 2.4 Hz), 7.49 (s, 1H), 7.46 (s, 1H), 7.34 (m, 1H), 7.23 (d, 1H, J=7.8 Hz), 7.06 (t, 1H, J=8.7 Hz), 4.27 (m, 1H), 3.40 (t, 2H, J=5.4 Hz), 3.19 (m, 1H), 3.01 (m, 3H), 2.67 (s, 6H), 2.65-2.35 (m, 10H), 2.26 (s, 3H), 2.07 (m, 2H), 1.81 (m, 2H). MS-ESI: 566.1 (M+H$^+$).

Preparative Example 24

Compound XXXI from Table 1

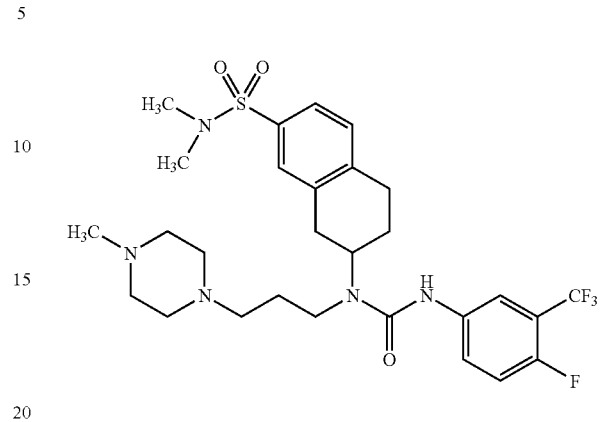

Following a similar procedure as in Preparative Example 9 except replacing 2-tetralone with 7-oxo-5,6,7,8-tetrahydro-naphthalene-2-sulfonic acid dimethylamide and replacing 3-chcloro-4-fluoro-phenylisocyanate with 3-trifluoromethyl-4-fluoro-phenylisocyanate, 0.050 g of 7-{3-(4-fluoro-3-trifluoromethyl-phenyl)-1-[3-(4-methyl-piperazin-1-yl)-propyl]-ureido}-5,6,7,8-tetrahydro-naphthalene-2-sulfonic acid dimethylamide was obtained as a white solid. $^1$H NMR (300 MHz, CDCl$_3$): δ 9.46 (s, 1H), 7.74 (m, 1H), 7.60 (dd, 1H, J=6.3, 2.7 Hz), 7.48 (m, 2H), 7.23 (d, 1H, J=7.8 Hz), 7.13 (t, 1H, J=9.6 Hz), 4.34 (m, 1H), 4.28 (m, 1H), 3.42 (t, 2H, J=5.4 Hz), 3.19 (m, 1H), 3.01 (m, 3H), 2.67 (s, 3H), 2.66 (s, 3H), 2.65-2.30 (m, 10H), 2.23 (s, 3H), 2.10 (m, 2H), 1.83 (m, 2H). MS-ESI: 600.1 (M+H$^+$).

Preparative Example 25

Compound XXXII from Table 1

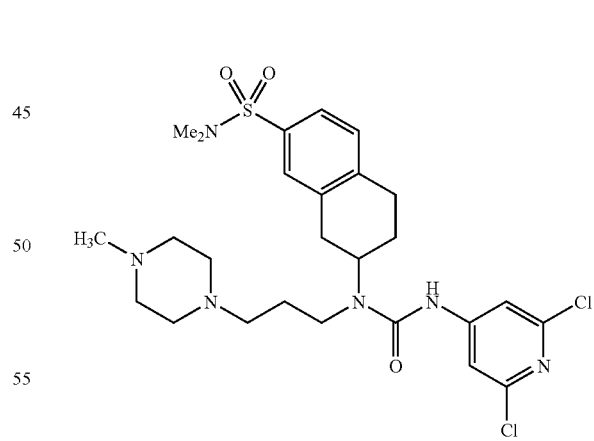

Following a similar procedure as in Preparative Example 9 except replacing 2-tetralone with 7-oxo-5,6,7,8-tetrahydro-naphthalene-2-sulfonic acid dimethylamide and replacing 3-chcloro-4-fluoro-phenylisocyante with 2,6-dichloro-4-isocyanato-pyridine, 0.050 g of 7-{3-(2,6-dichloro-pyridin-4-yl)-1-[3-(4-methyl-piperazin-1-yl)-propyl]-ureido NMR (300 MHz, CD$_3$OD): δ 7.59 (s, 2H), 7.53 (s, 1H), 7.51 (d, 1H, J=7.8 Hz), 7.35 (d, 1H, J=7.8 Hz), 4.30 (m, 1H), 3.44 (t, 2H, J=7.5 Hz), 3.22 (m, 1H), 3.04 (m, 3H), 2.66 (s, 6H), 2.65-2.40 (m, 10H), 2.31 (s, 3H), 2.09 (m, 2H), 1.88 (m, 2H). MS-ESI: 583.2 (M+H$^+$).

Preparative Example 26

Compound II from Table 1

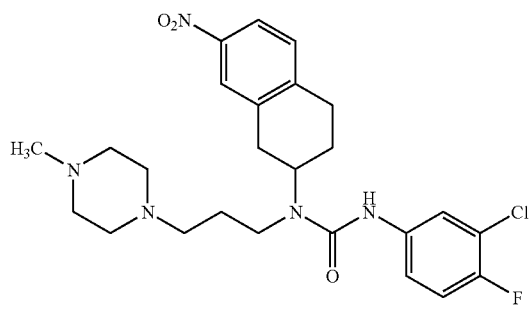

Following a similar procedure as in Preparative Example 9 except replacing 2-tetralone with 7-nitro-2-tetralone (prepared according to the procedure by J. B. Nevy, et al., J. Am. Chem. Soc., 1997, 119, 12722-6), 0.61 g of 3-(3-chloro-4-fluoro-phenyl)-1-[3-(4-methyl-piperazin-1-yl)-propyl]-1-(7-nitro-1,2,3,4-tetrahydro-naphthalen-2-yl)-urea was obtained as a yellow solid. $^1$H NMR (300 MHz, CD$_3$OD): δ 8.05 (s, 1H), 8.02 (dd, 1H), 7.67 (dd, 1H), 7.42 (m, 1H), 7.39 (d, 1H), 7.25 (t, 1H), 4.42 (m, 1H), 3.52 (t, 2H), 3.28 (m, 1H), 3.15 (m, 3H), 2.75-2.45 (m, 10H), 2.36 (s, 3H), 2.18 (m, 2H), 1.96 (m, 2H). MS-ESI: 504.1 (M+H$^+$).

Preparative Example 27

Compound XIV from Table 1

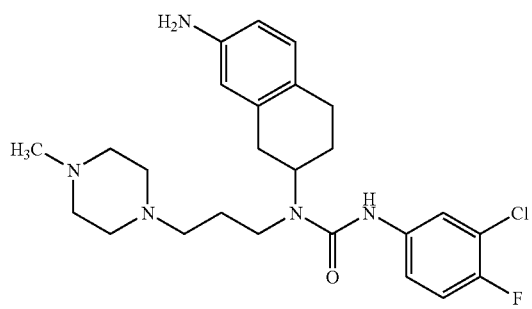

To a solution of 3-(3-chloro-4-fluoro-phenyl)-1-[3-(4-methyl-piperazin-1-yl)-propyl]-1-(7-nitro-1,2,3,4-tetrahydro-naphthalen-2-yl)-urea (from Preparative Example 26, 0.286 g, 0.57 mmol) in absolute EtOH (10 mL) was added Raney Ni (~50 mg). The mixture was hydrogenated using a Parr hydrogenator at 50 psi for 2 hours, then filtered through Celite, and the filtrate was concentrated in vacuo. The residue was purified by silica gel chromatography by eluting with 5% MeOH/CH$_2$Cl$_2$ to give 0.200 g (75%) of 1-(7-amino-1,2,3,4-tetrahydro-naphthalen-2-yl)-3-(3-chloro-4-fluoro-phenyl)-1-[3-(4-methyl-piperazin-1-yl)-propyl]-urea as a light brown solid. $^1$H NMR (300 MHz, CD$_3$OD): δ 7.57 (dd, 1H), 7.31 (m, 1H), 7.15 (t, 1H), 6.84 (d, 1H), 6.53 (dd, 1H), 6.48 (d, 1H), 4.30 (m, 1H), 3.38 (t, 2H), 2.95 (m, 1H), 2.82 (m, 3H), 2.60-2.35 (m, 10H), 2.26 (s, 3H), 1.96 (m, 2H), 1.85 (m, 2H). MS-ESI: 474.1 (M+H$^+$).

Preparative Example 28

Compound I from Table 1

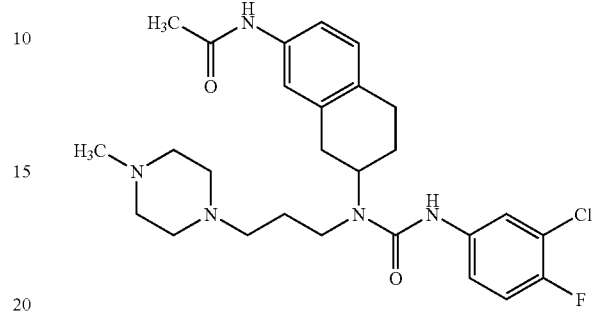

To a solution of 1-(7-amino-1,2,3,4-tetrahydro-naphthalen-2-yl)-3-(3-chloro-4-fluoro-phenyl)-1-[3-(4-methyl-piperazin-1-yl)-propyl]-urea (from Preparative Example 27, 0.033 g, 0.070 mmol) in CH$_2$Cl$_2$ (0.2 mL) at 0° C. were added Ac$_2$O (0.0066 mL, 0.070 mmol) and DIEA (0.036 mL, 0.21 mmol). The mixture was stirred from 0° C. to room temperature for 16 hours. The mixture was concentrated in vacuo and the residue was purified by preparative HPLC to give 0.030 g (83%) of N-(7-{3-(3-chloro-4-fluoro-phenyl)-1-[3-(4methyl-piperazin-1-yl)-propyl]-ureido}-5,6,7,8-tetrahydro-naphthalen-2yl)-acetam ide as a light yellow gum. $^1$H NMR (300 MHz, CD$_3$OD): δ 7.60 (dd, 1H, J=6.9, 2.4 Hz), 7.38 (d, 1H, J=2.1 Hz), 7.30 (ddd, 1H, J=9.0, 4.2, 2.4 Hz), 7.20 (dd, 1H, J=8.4, 2.1 Hz), 7.15 (t, 1H, J=9.0 Hz), 7.05 (d, 1H, J=8.4 Hz), 4.31 (m, 1H), 3.60 (m, 8H), 3.47 (m, 2H), 3.24 (t, 2H, J=7.2 Hz), 2.97 (m, 7H), 2.14-2.00 (m, 7H). MS-ESI: 516.1 (M+H$^+$).

Preparative Example 29

Compound IV from Table 1

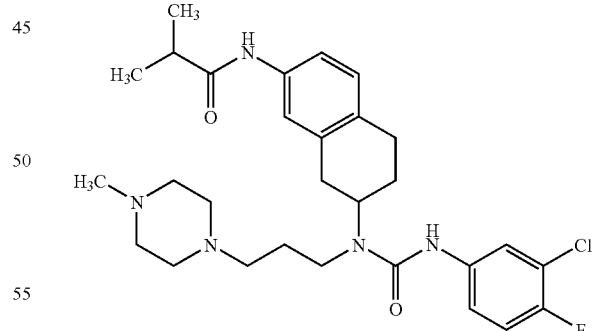

To a solution of 1-(7-amino-1,2,3,4-tetrahydro-naphthalen-2-yl)-3-(3-chloro-4-fluoro-phenyl)-1-[3-(4-methyl-piperazin-1-yl)-propyl]-urea (Preparative Example 27, 0.020 g, 0.042 mmol) in CH$_2$Cl$_2$ (0.2 mL) at 0° C. were added isobutyryl chloride (0.0054 mL, 0.052 mmol) and DIEA (0.026 mL, 0.15 mmol). After stirring from 0° C. to room temperature for 16 hours, the mixture was concentrated in vacuo and the residue was purified by preparative HPLC to give 0.020 g (88%) of N-(7-{3-(3-chloro-4-fluoro-phenyl)-1-[3-(4-methyl-piperazin-1-yl)-propyl]-ureido}-5,6,7,8-tetrahydro-naphthalen-2-yl)-isobutyramide as a light yellow gum. $^1$H NMR (300 MHz, CD$_3$OD): δ 7.60 (dd, 1H, J=6.9, 2.4 Hz), 7.40 (d, 1H, J=2.1 Hz), 7.30 (ddd, 1H, J=9.0, 4.2, 2.4 Hz), 7.20 (dd, 1H, J=8.4, 2.1 Hz), 7.15 (t, 1H, J=9.0 Hz), 7.05 (d, 1H, J=8.4 Hz), 4.31 (m, 1H), 3.62 (m, 8H), 3.49 (m, 2H), 3.27 (t, 2H, J=6.9 Hz), 2.98 (m, 7H), 2.10 (m, 4H), 1.38 (dd, 1H, J=6.6, 2.7 Hz), 1.19 (d, 6H, J=6.6 Hz). MS-ESI: 544.1 (M+H$^+$).

Preparative Example 30

Compound IX from Table 1

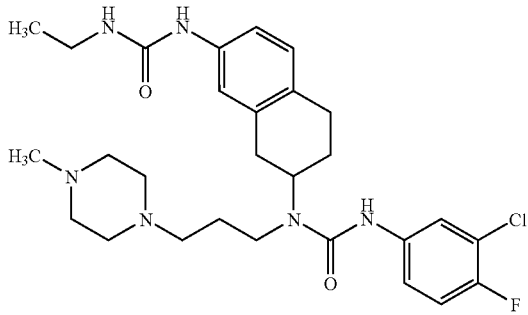

To a solution of 1-(7-amino-1,2,3,4-tetrahydro-naphthalen-2-yl)-3-(3-chloro-4-fluoro-phenyl)-1-[3-(4-methyl-piperazin-1-yl)-propyl]-urea (from Preparative Example 27, 0.018 g, 0.038 mmol) in CH$_2$Cl$_2$ (0.2 mL) at 0° C. was added ethylisocyanate (0.0030 mL, 0.038 mmol). The mixture was stirred from 0° C. to room temperature for 16 hours, then concentrated in vacuo, and the residue was purified by preparative HPLC to give 0.019 g (92%) of 1-(7-{3-(3-chloro-4-fluoro-phenyl)-1-[3-(4-methyl-piperazin-1-yl)-propyl]-ureido}-5,6,7,8-tetrahydro-naphthalen-2-yl)-3-ethyl-urea as a light yellow gum. $^1$H NMR (300 MHz, CD$_3$OD): δ 7.60 (dd, 1H, J=6.6, 2.4 Hz), 7.30 (ddd, 1H, J=9.0, 4.2, 2.7 Hz), 7.18 (s, 1H), 7.15 (t, 1H, J=9.0 Hz), 7.06-6.97 (m, 2H), 4.30 (m, 1H), 3.60-3.40 (m, 10H), 3.20 (m, 4H), 3.05-2.85 (m, 7H), 2.07 (m, 4H), 1.15 (t, 3H, J=7.5 Hz). MS-ESI: 545.0 (M+H$^+$).

Preparative Example 31

Compound VIII from Table 1

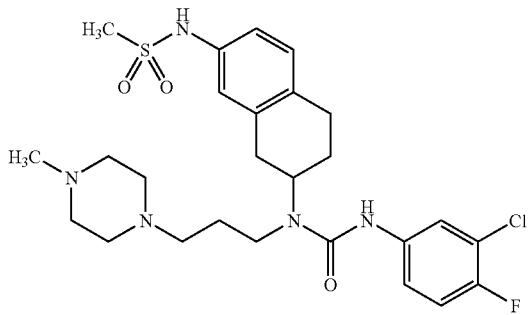

To a solution of 1-(7-amino-1,2,3,4-tetrahydro-naphthalen-2-yl)-3-(3-chloro-4-fluoro-phenyl)-1-[3-(4-methyl-piperazin-1-yl)-propyl]-urea (from Preparative Example 27, 0.035 g, 0.074 mmol) in CH$_2$Cl$_2$ (0.2 mL) at 0° C. were added methanesulfonyl chloride (0.0058 mL, 0.074 mmol) and DIEA (0.039 mL, 0.22 mmol). The mixture was stirred from 0° C. to room temperature for 3 hours, then concentrated in vacuo, and the residue was purified by preparative HPLC to give 0.035 g (88%) of N-(7-{3-(3-chloro-4-fluoro-phenyl)-1-[3-(4-methyl-piperazin-1-yl)-propyl]-ureido}-5,6,7,8-tetrahydro-naphthalen-2-yl)-methanesulfonamide as a light yellow gum. $^1$H NMR (300 MHz, CD$_3$OD): δ 7.59 (dd, 1H, J=6.6, 2.7 Hz), 7.30 (ddd, 1H, J=9.0, 4.2, 2.7 Hz), 7.14 (t, 1H, J=9.0 Hz), 7.08 (d, 1H, J=8.4 Hz), 7.04-6.98 (m, 2H), 4.30 (m, 1H), 3.66 (m, 8H), 3.46 (m, 2H), 2.99 (m, 6H), 2.90 (s, 3H), 2.11 (m, 4H). MS-ESI: 552.0 (M+H$^+$).

Preparative Example 32

Compound III from Table 1

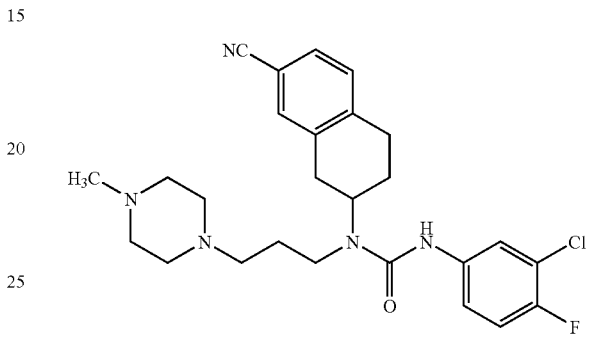

To a solution of 1-(7-amino-1,2,3,4-tetrahydro-naphthalen-2-yl)-3-(3-chloro-4-fluoro-phenyl)-1-[3-(4-methyl-piperazin-1-yl)-propyl]-urea (from Preparative Example 27, 0.061 g, 0.13 mmol) in 18% aqueous HCl (0.077 mL) at 0° C. was added, slowly, a solution of NaNO$_2$ (9.4 mg, 0.14 mmol) in H$_2$O (0.091 mL) over 30 min. The mixture was neutralized with Na$_2$CO$_3$ (powder) followed by the addition of a solution of CuCN (0.012 g, 0.13 mmol) and NaCN (14 mg, 0.28 mmol) in H$_2$O (0.091 mL). The mixture was then heated at 50° C. for 30 min. The reaction was concentrated in vacuo and the crude residue was purified on reverse-phase HPLC to give 0.015 g (24%) of 3-(3-chloro-4-fluoro-phenyl)-1-(7-cyano-1,2,3,4-tetrahydro-naphthalen-2-yl)-1-[3-(4-methyl-piperazin-1-yl)-propyl]-urea as a white solid. $^1$H NMR (300 MHz, CD$_3$OD): □ 7.59 (dd, 1H, J=6.6, 2.7 Hz), 7.50 (s, 1H), 7.46 (dd, 1H, J=8.1, 1.5 Hz), 7.34-7.26 (m, 2H), 7.16 (t, 1H, J=9.0 Hz), 4.31 (m, 1H), 3.55-3.35 (m, 10H), 3.15-3.00 (m, 6H), 2.92 (s, 3H), 2.05 (m, 4H). MS-ESI: 484.1 (M+H$^+$).

Preparative Example 33

Compound XXV from Table 1

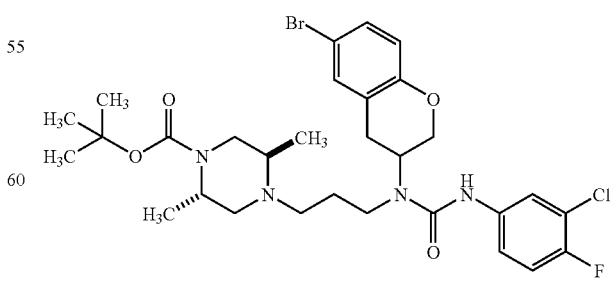

A mixture of 6-bromo-chroman-3-ylamine (0.105 g, 0.46 mmol, 1 eq), (2S,5R)-4-(3-chloro-propyl)-2,5-dimethyl-piperazine-1-carboxylic acid tert-butyl ester (0.133 g, 0.46 mmol, 1 eq), $K_2CO_3$ (0.127 g, 0.92 mmol, 2 eq), and KI (0.017 g, 0.10 mmol, 0.2 eq) in DMF (0.5 mL) was heated in a microwave reactor at 150° C. for 25 min. The reaction mixture was partitioned between EtOAc (3 mL) and 10% aqueous $NaHCO_3$ (3 mL). The organic layer was separated and aqueous layer was extracted with EtOAc (2 mL×3). The combined organic layers were dried ($Na_2SO_4$) and concentrated in vacuo to give 0.22 g (100%) of (2S,5R)-4-[3-(6-bromo-chroman-3-ylamino)-propyl]-2,5-dimethyl-piperazine-1-carboxylic acid tert-butyl ester as a yellow oil. The material was carried on to next step without further purification.

To a solution of (2S,5R)-4-[3-(6-bromo-chroman-3-ylamino)-propyl]-2,5-dimethyl-piperazine-1-carboxylic acid tert-butyl ester (0.12 g, 0.25 mmol) in $CH_2Cl_2$ (0.5 mL) was added 3-chloro-4-fluoro-phenylisocyanate (0.043 g, 0.25 mmol). After stirring at room temperature for 16 hours, the mixture was concentrated in vacuo and the residue was purified on reverse-phase HPLC to give 0.047 g (29%) of (2S,5R)-4-{3-[1-(6-bromo-chroman-3-yl)-3-(3-chloro-4-fluoro-phenyl)-ureido]-propyl}-2,5-dimethyl-piperazine-1-carboxylic acid tert-butyl ester as a white solid. $^1$H NMR (300 MHz, $CDCl_3$): δ 7.85 (d, J=17.4 Hz, 1H), 7.62 (d, J=6.3 Hz, 1H), 7.23 (m, 2H), 7.02 (t, J=9.0 Hz, 1H), 6.71 (d, J=9.0 Hz, 1H), 6.14 (br.s, 1H), 4.55 (m, 2H), 4.26 (m, 2H), 3.92 (m, 1H), 3.60-2.70 (m, 10H), 2.05 (m, 2H), 1.46 (s, 9H), 1.37 (d, J=7.2 Hz, 3H), 1.20 (m, 3H). MS-ESI: 653.1 (M+H$^+$).

Preparative Example 34

Compound XVIII from Table 1

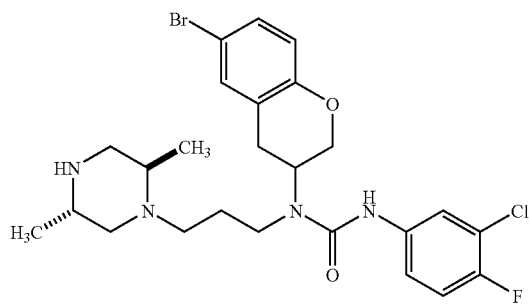

(2S,5R)-4-{3-[1-(6-bromo-chroman-3-yl)-3-(3-chloro-4-fluoro-phenyl)-ureido]-propyl}-2,5-dimethyl-piperazine-1-carboxylic acid tert-butyl ester (0.053 g, 0.081 mmol) was treated with 20% TFA/$CH_2Cl_2$ (0.4 mL) at room temperature for 2 hours. The reaction mixture was diluted with toluene (4 mL) and concentrated in vacuo. Purification on reverse-phase HPLC gave 0.043 g (96%) of (2R,5S)-1-(6-bromo-chroman-3-yl)-3-(3-chloro-4-fluoro-phenyl)-1-[3-(2,5-dimethyi-piperazin-1-yl)-propyl]-urea as a white solid. $^1$H NMR (300 MHz, $CD_3OD$): □ 7.83 (dd, J=6.6, 2.4 Hz, 1H), 7.53 (m, 2H), 7.45 (dd, J=8.7, 2.4 Hz, 1H), 7.38 (t, J=9.0 Hz, 1H), 6.98 (d, J=9.0 Hz, 1H), 4.71 (m, 1H), 4.46 (m, 2H), 4.07 (m, 1H), 4.00-3.20 (m, 10H), 2.26 (m, 2H), 1.66 (d, J=6.2 Hz, 3H), 1.63 (d, J=6.6 Hz, 3H). MS-ESI: 553.0 (M+H$^+$).

By analogy to the procedures of Preparative Examples 33 and 34, Example Numbers 5, 11, 15, 18, 21, 23, 25 and 26 of Table 1 were prepared.

In still another embodiment of the present invention, a compound is selected from the following structures in Table 1 below (or pharmaceutically acceptable salts or solvates thereof) which are shown along with their Ki ratings.

Compounds with Ki values greater than about 2 μM are designated in Table 1 below as C class compounds.

Compounds with Ki values between about 1 and 2 μM are designated in Table 1 below as B class compounds.

Compounds with Ki values less than about 1 μM are designated in Table 1 below as A class compounds.

In a preferred embodiment of the invention, Compound I of Table 1 has a Ki value of 0.006 μM was observed. The Ki values for Compounds II-X, are described below:

| Compound | Ki |
|---|---|
| I | 0.006 |
| II | 0.011 |
| III | 0.014 |
| IV | 0.061 |
| V | 0.063 |
| VI | 0.065 |
| VII | 0.092 |
| VIII | 0.096 |
| IX | 0.157 |
| X | 0.178 |

MCH Receptor Binding Assay:

Membranes from CHO cells expressing the MCH receptor were prepared by lysing cells with 5 mM HEPES for 15 minutes at 4° C. Cell lysates were centrifuged (12.5000×g, 15 minutes) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 minutes at 4° C. in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4X the desired final concentration). Nonspecific binding was determined by including 1 μM MCH in the binding reaction. The binding reaction was incubated at room temperature for 2 hours. Plates were then analyzed in a TOPCOUNT microplate scintillation counter (Packard). Data was analyzed and Ki values were determined using GraphPad Prism.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE 1

| Compound Number | Structure | Ki μM |
|---|---|---|
| I | 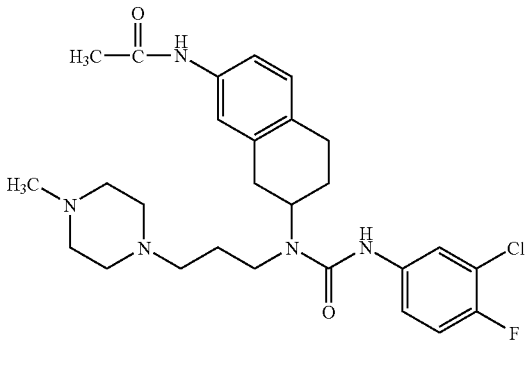 | A |
| II | 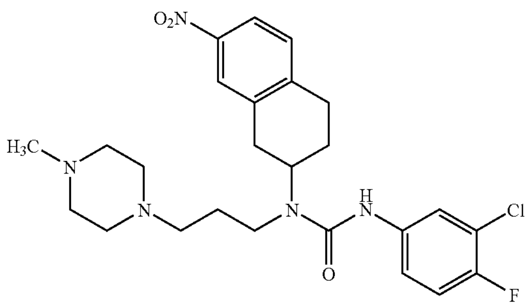 | A |
| III | 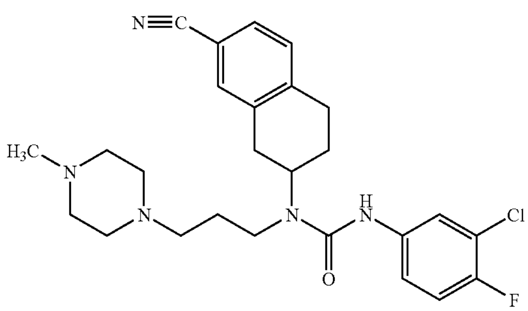 | A |
| IV | 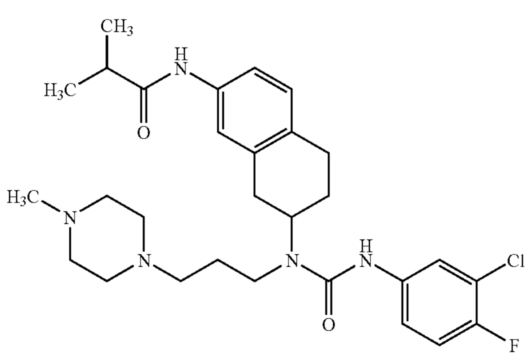 | A |

TABLE 1-continued

| Compound Number | Structure | Ki µM |
|---|---|---|
| V | 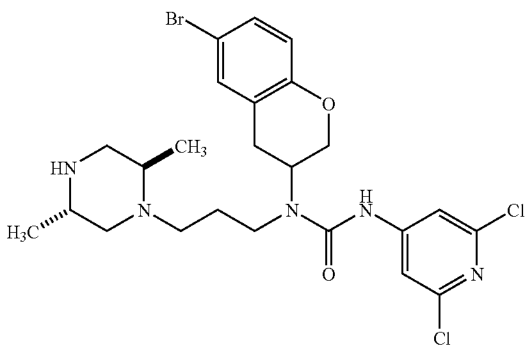 | A |
| VI | 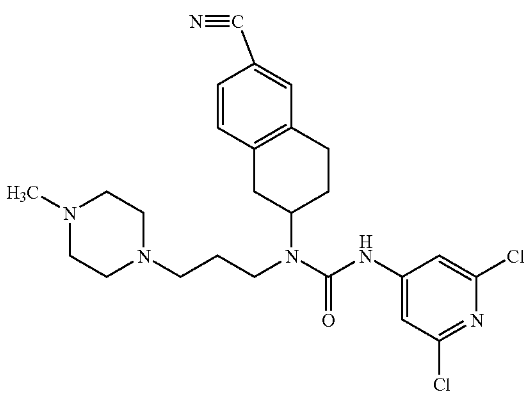 | A |
| VII | 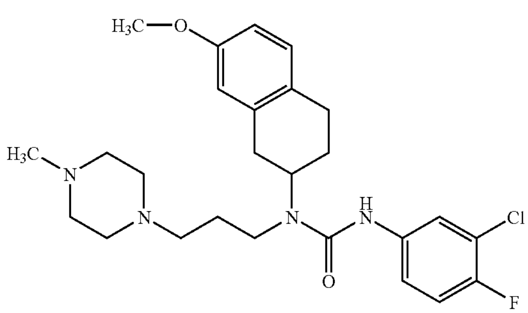 | A |
| VIII | 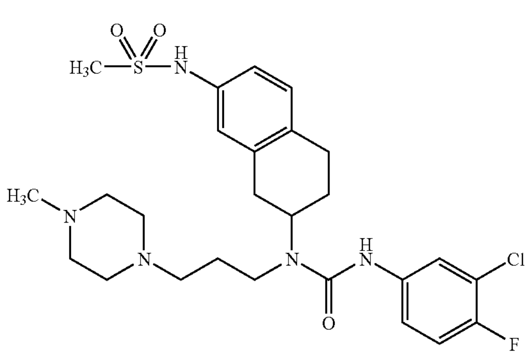 | A |

TABLE 1-continued
| Compound Number | Structure | Ki μM |
|---|---|---|
| IX | 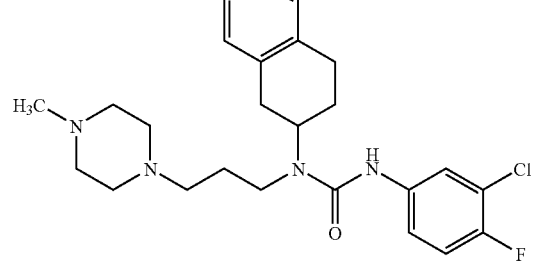 | A |
| X | 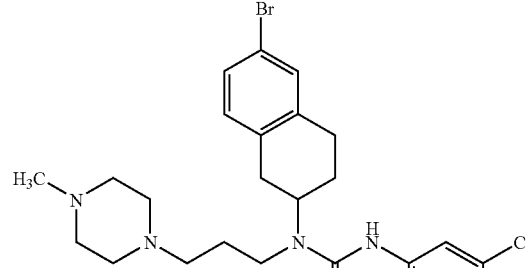 | A |
| XI | 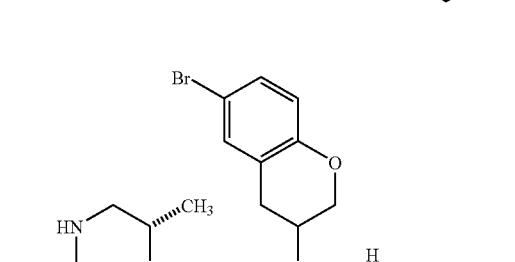 | A |
| XII | 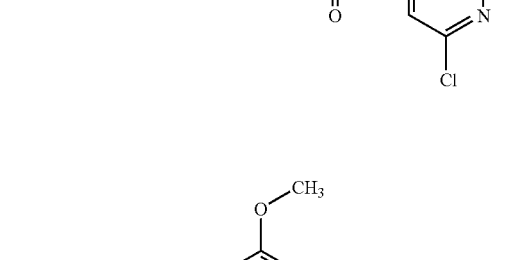 | A |

TABLE 1-continued

| Compound Number | Structure | Ki µM |
|---|---|---|
| XIII | 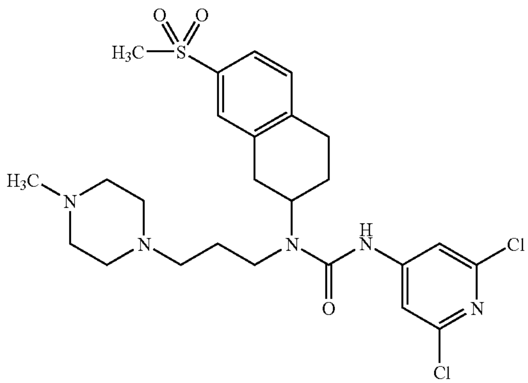 | A |
| XIV | 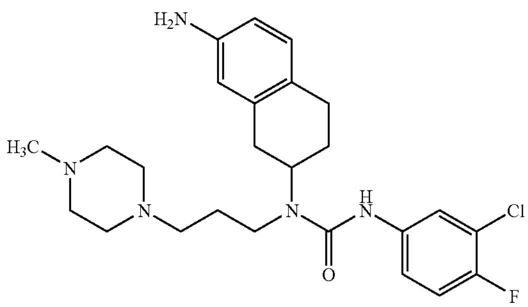 | A |
| XV | 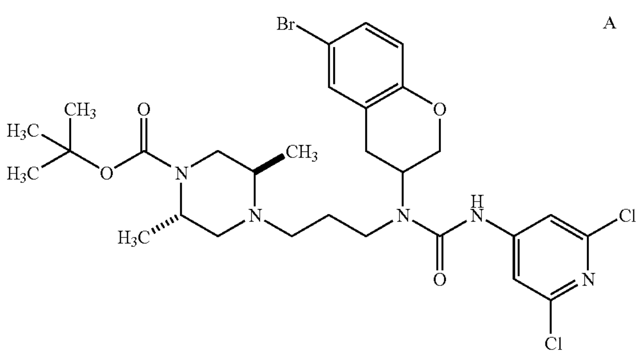 | A |
| XVI | 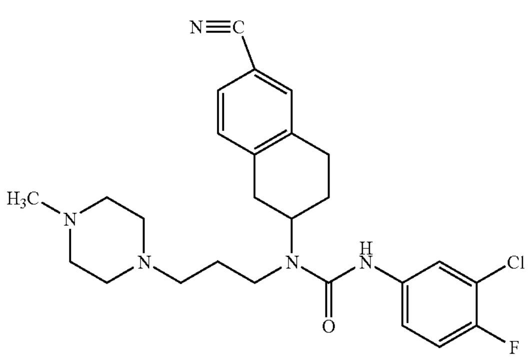 | A |

TABLE 1-continued

| Compound Number | Structure | Ki μM |
|---|---|---|
| XVII | 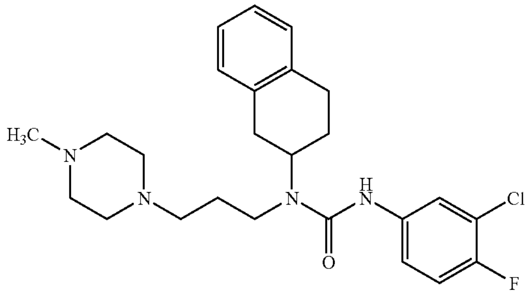 | A |
| XVIII | 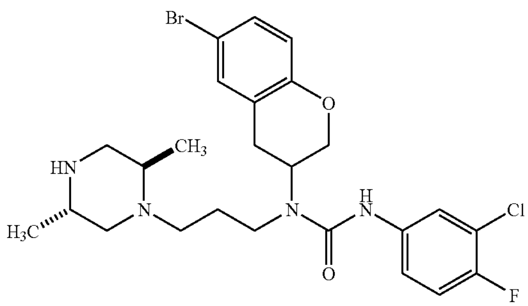 | A |
| XIX | 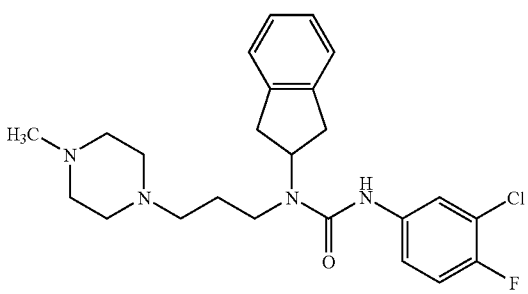 | A |
| XX | 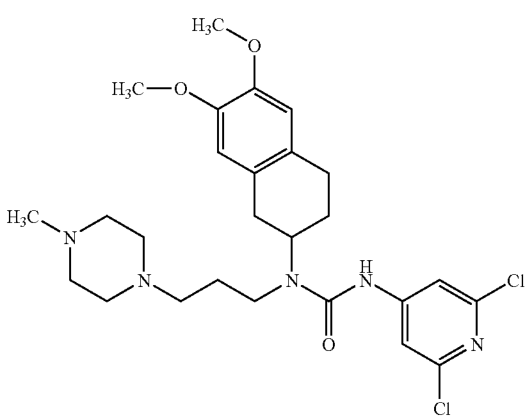 | A |

TABLE 1-continued
| Compound Number | Structure | Ki μM |
|---|---|---|
| XXI | 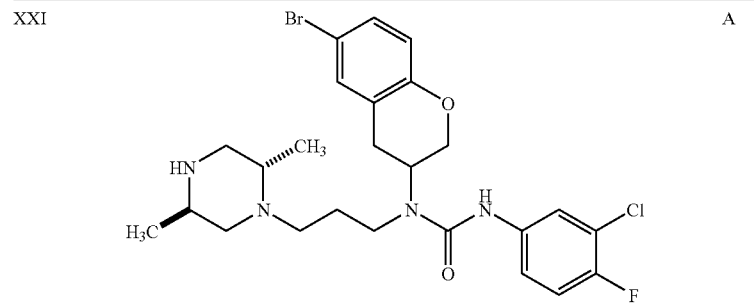 | A |
| XXII | 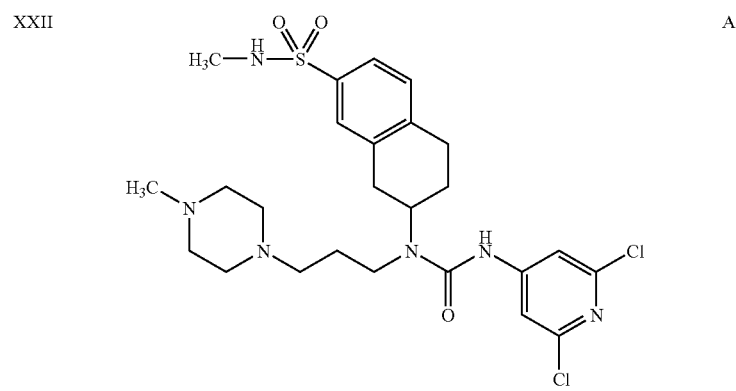 | A |
| XXIII | 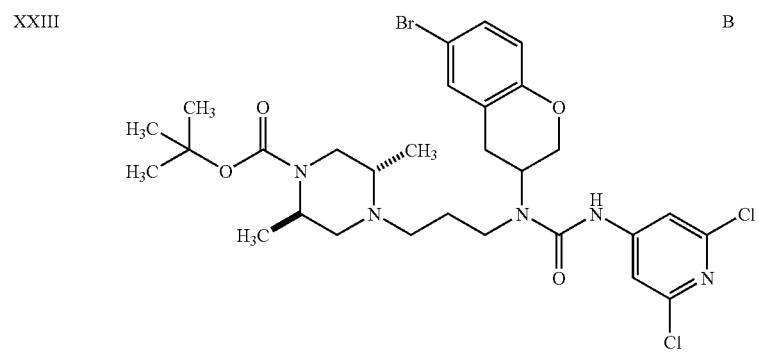 | B |
| XXIV | 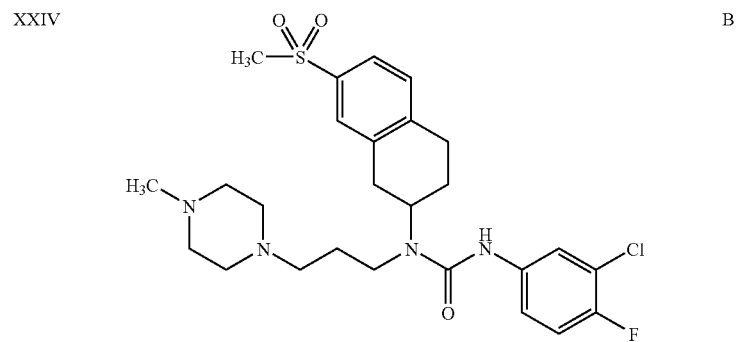 | B |

TABLE 1-continued
| Compound Number | Structure | Ki μM |
|---|---|---|
| XXV | 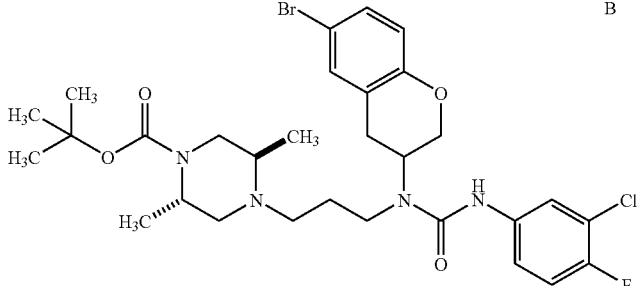 | B |
| XXVI | 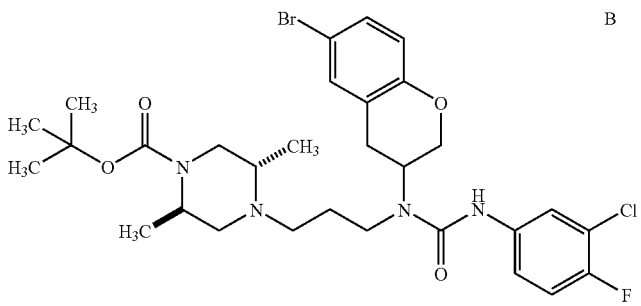 | B |
| XXVII | 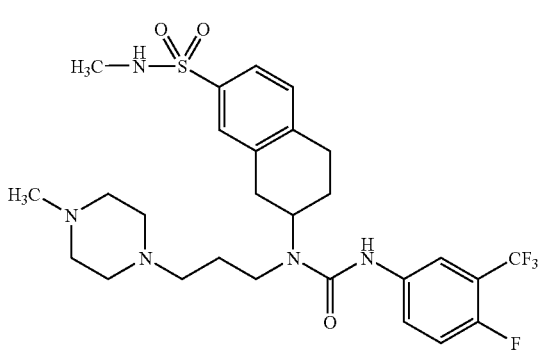 | B |
| XXVIII | 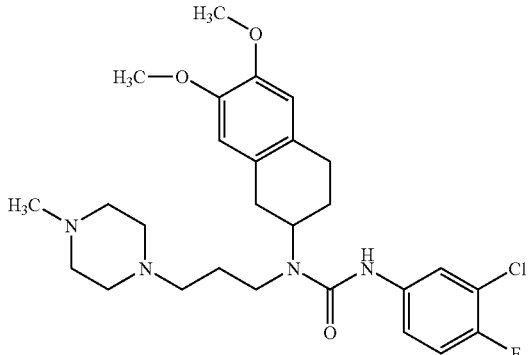 | C |

TABLE 1-continued

| Compound Number | Structure | Ki μM |
|---|---|---|
| XIX | 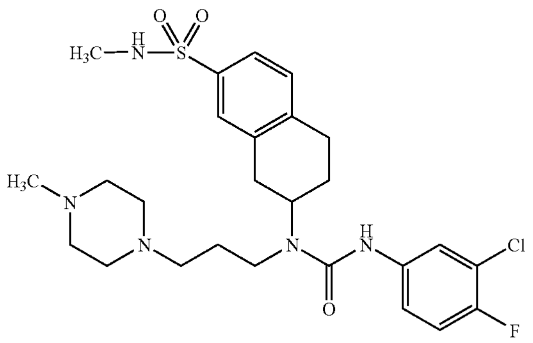 | C |
| XXX | 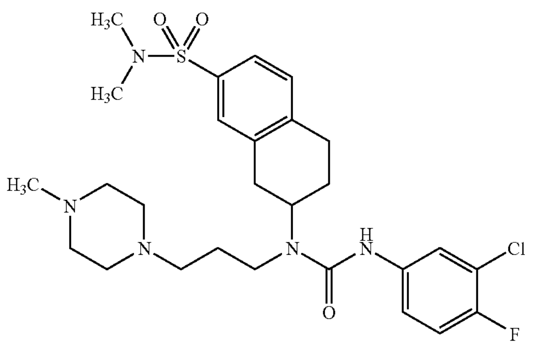 | C |
| XXXI | 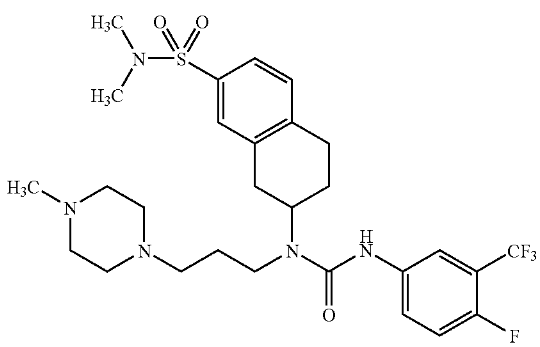 | C |
| XXXII | 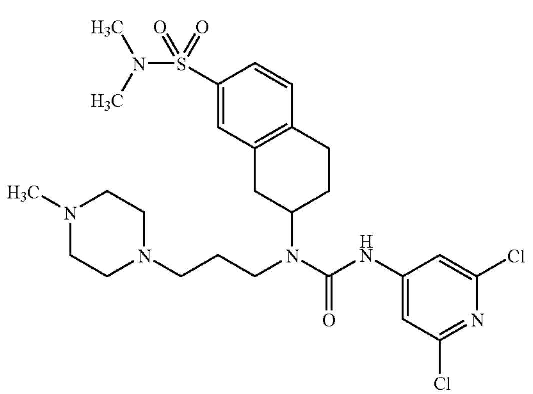 | C |

What is claimed is:

1. A compound, having the general structure represented by structural Formula 1:

Formula 1 or a pharmaceutically acceptable salt thereof wherein:
Ar is $(R^{19})_q$-substituted phenyl or $(R^{19})_q$-substituted pyridyl;
$R^3$ is independently selected at each occurrence thereof from the group consisting of: H, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, keto, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), -alkyl-NR$^{17}$R$^{18}$, —C(=O)NR$^{17}$R$^{18}$, —NR$^{17}$R$^{18}$, —NHC(=O)R$^{17}$, —NHC(=O)OR$^{17}$, —NHC(=O)NR$^{17}$R$^{18}$, —NHS(O)$_2$ R$^{17}$, —NHS(O)$_2$NR$^{17}$R$^{18}$, —S(O)R$^{17}$, —S(O)$_2$R$^{17}$ and S(O)$_2$NR$^{17}$R$^{18}$;
or two $R^3$ moieties on adjacent carbons can be linked together to form a 4 to 6 membered cycloalkyl or 4 to 6 membered heterocyclyl group, with the proviso that there are no adjacent oxygen or sulfur atoms present in the heterocyclyl group, wherein the cycloalkyl and heterocyclyl groups are fused to the ring carbons to which $R^3$ is attached;
$R^{12}$ is independently selected at each occurrence thereof from the group consisting of: H, alkyl, cycloalkyl, alkoxyalkyl, hydroxyalkyl and cycloalkoxyalkyl;
$R^{13}$ is H, alkyl, aryl, heteroaryl, alkoxyalkyl, hydroxyalkyl, acyl, alkoxycarbonyl, cycloalkoxyalkyl, carbamoyl, arylsulfonyl, alkylsulfonyl or —CN;
$R^{17}$ and $R^{18}$ are each independently selected at each occurrence thereof and are each independently H, alkyl, cycloalkyl, aryl, heteroalkyl and heteroarylalkyl;
$R^{19}$ is independently selected at each occurrence thereof from the group consisting of: H, alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), —NR$^{17}$R$^{18}$, -alkyl-NR$^{17}$R$^{18}$, —C(=O)NR$^{17}$R$^{18}$, —NHC(=O)R$^{17}$, —NHC(=O)OR$^{17}$, —NHC(=O)NR$^{17}$R$^{18}$, —NHS(O)$_2$ R$^{17}$, —NHS(O)$_2$NR$^{17}$R$^{18}$, —S(O)$_2$NR$^{17}$R$^{18}$, and —S(O)$_2$NR$^{17}$R$^{18}$;
r is 1, 2, 3 or 4;
q is 1, 2 or 3; and
t is 1 or 2.

2. The compound according to claim 1, wherein $R^3$ is independently selected from the group consisting of: H, halogen, alkyl, alkoxy, —NH$_2$, —CN, —NO$_2$, —NHS(O)$_2$R$^{17}$, —NHC(=O)NR$^{17}$R$^{18}$, —S(O)$_2$R$^{17}$ and —NHC(=O)R$^{17}$;
or two $R^3$ moieties on adjacent carbons are linked together to form 3. The compound according to claim 1, wherein $R^3$ is independently selected from the group consisting of: H, halogen, alkyl, alkoxy, —NHC(=O)alkyl, —NO$_2$, NH$_2$, —CN, —NHC(=O)NHalkyl and —S(O)$_2$alkyl.

4. The compound according to claim 1, wherein $R^{13}$ is H, alkyl, acyl, alkoxycarbonyl, carbamoyl, arylsulfonyl or —CN.

5. The compound according to claim 1, wherein $R^{13}$ is H, alkyl or alkoxycarbonyl.

6. The compound according to claim 1, wherein $R^{17}$ is independently selected at each occurrence thereof from the group consisting of: H, —CH$_3$, —CH(CH$_3$)$_2$ or —CH$_2$CH$_3$.

7. The compound according to claim 1, wherein $R^{18}$ is independently selected at each occurrence thereof from the group consisting of: H, —CH$_3$, —CH(CH$_3$)$_2$ or —CH$_2$CH$_3$.

8. The compound according to claim 1, wherein $R^{19}$ is independently selected at each occurrence thereof from the group consisting of: H, halogen, and —CN.

9. The compound according to claim 1, wherein q is 2.

10. The compound according to claim 1, wherein r is 1 or 2.

11. The compound according to claim 1, wherein t is 2.

12. The compound according to claim 1, having the general structure represented by structural Formula 3:

Formula 3 or a pharmaceutically acceptable salt thereof wherein X is CH, CF or N.

13. The compound according to claim 12, wherein:

R³ is independently selected at each occurrence thereof from the group consisting of: H, halogen, alkyl, alkoxy, —NH₂, —CN, —NO₂, —NHS(O)₂R¹⁷, —NHC(=O)NR¹⁷R¹⁸, —S(O)₂R¹⁷ and —NHCOR¹⁷;

R¹² is independently selected at each occurrence thereof from the group consisting of: H and alkyl;

R¹³ is H, alkyl or —C(=O)Oalkyl;

R¹⁹ is independently selected at each occurrence thereof and is —H, or halogen;

X is CF or N; and r and t are 2.

14. A compound of Formula I selected from the group consisting of:

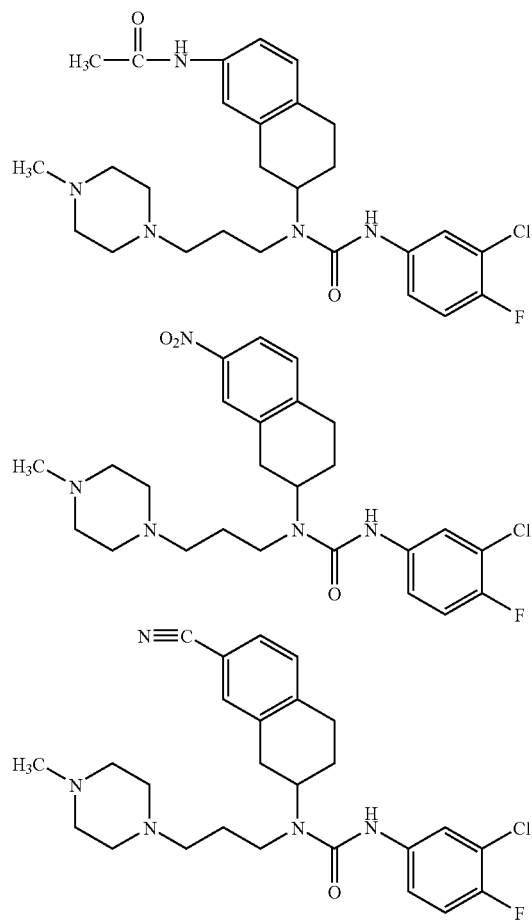

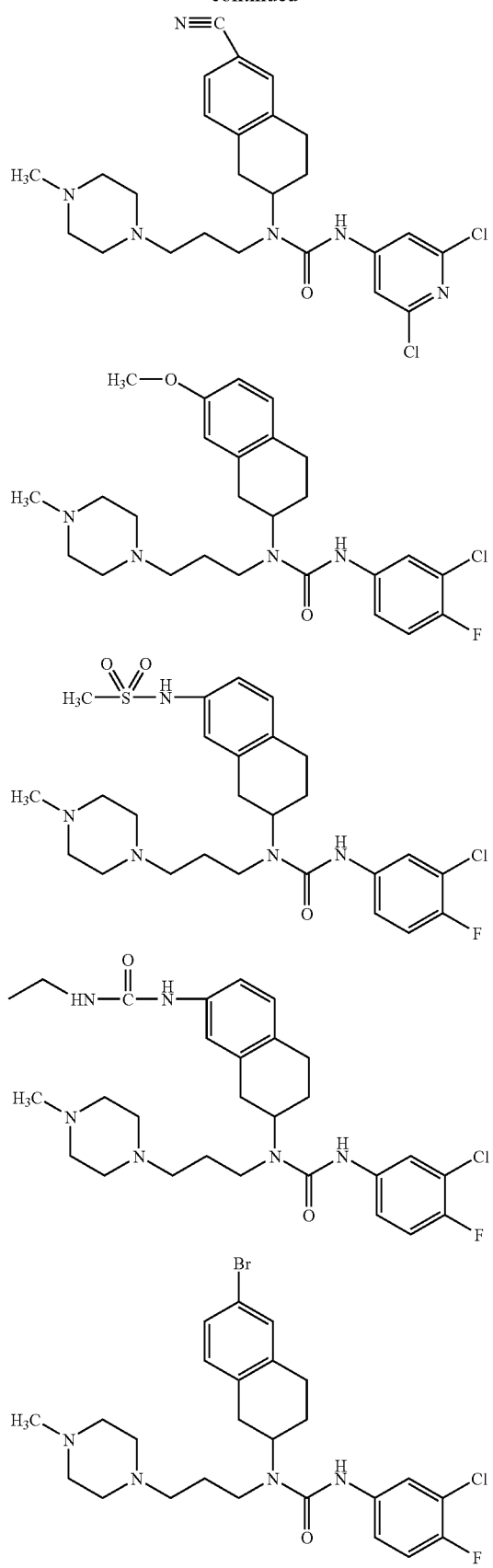

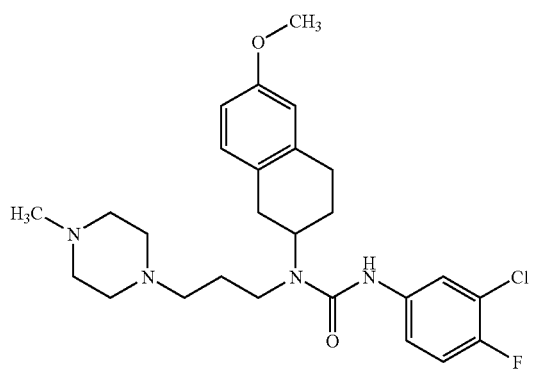
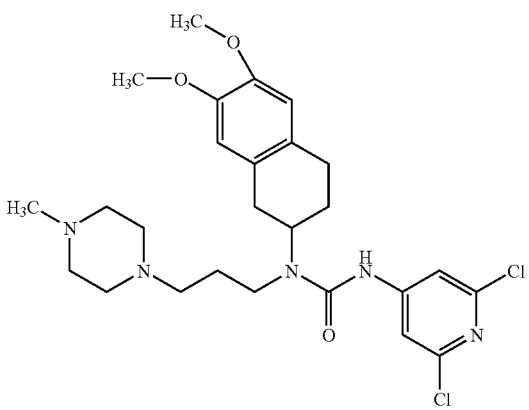
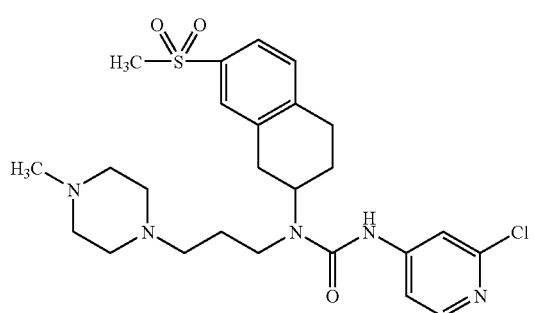
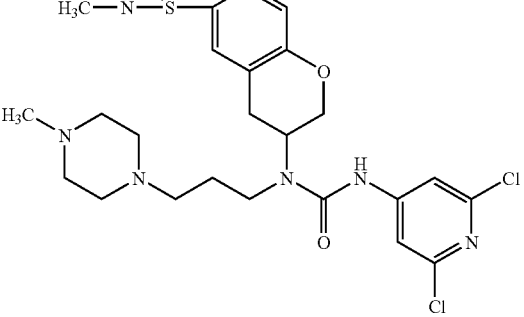
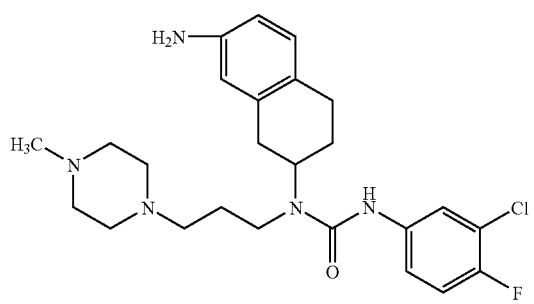
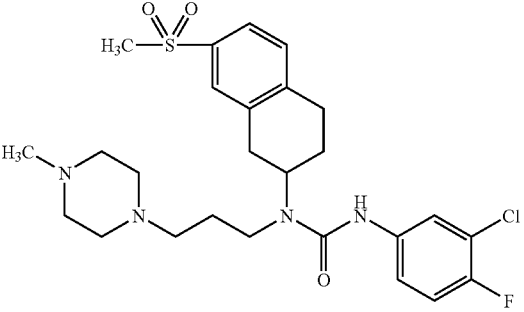
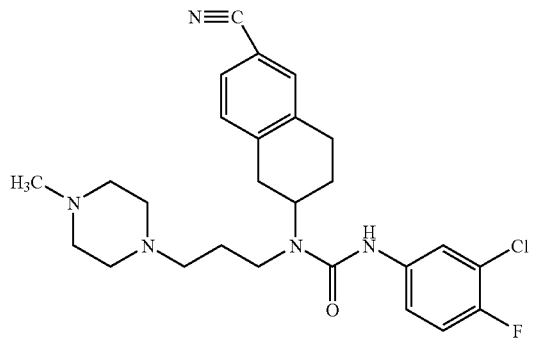
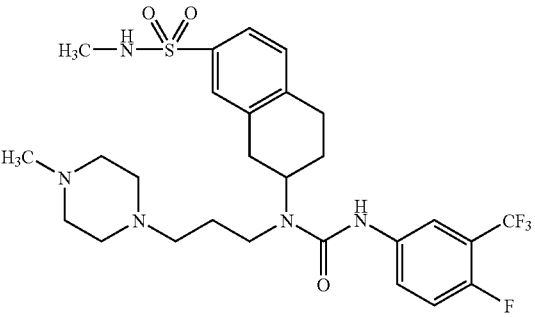
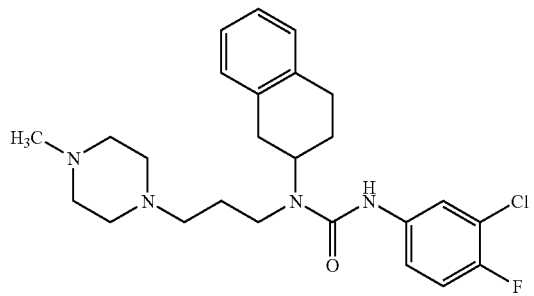

-continued
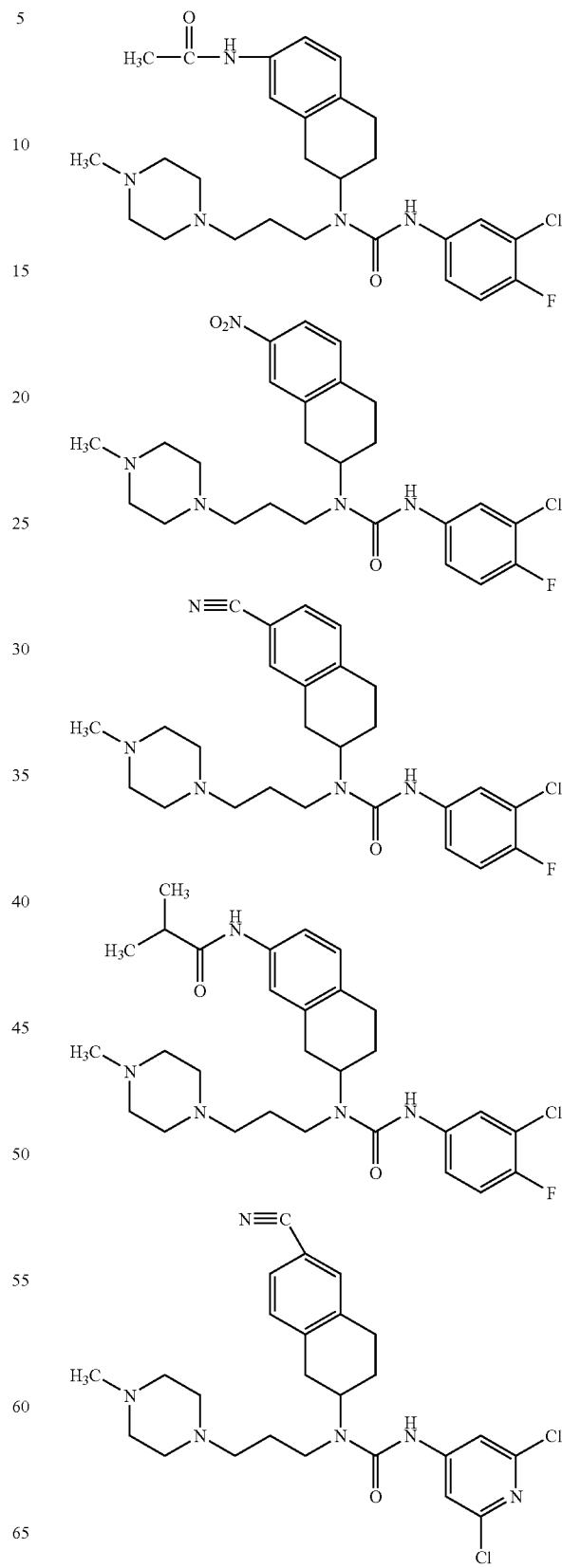
15. A compound of Formula I selected from the group consisting of:
or a pharmaceutically acceptable salt thereof.

-continued

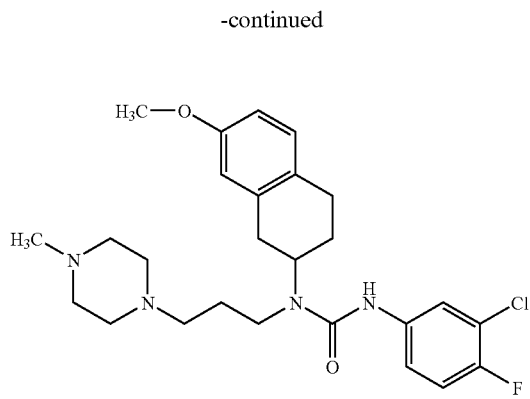

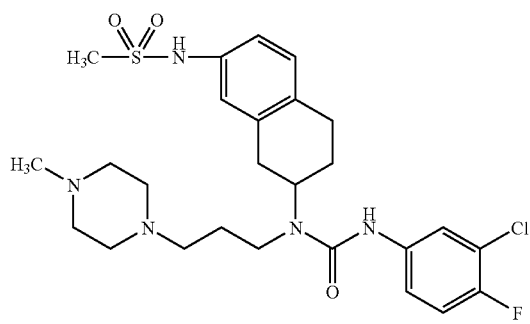

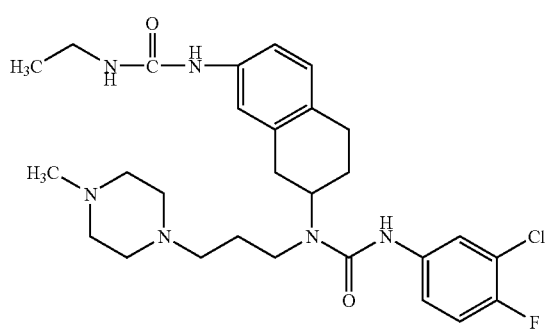

-continued

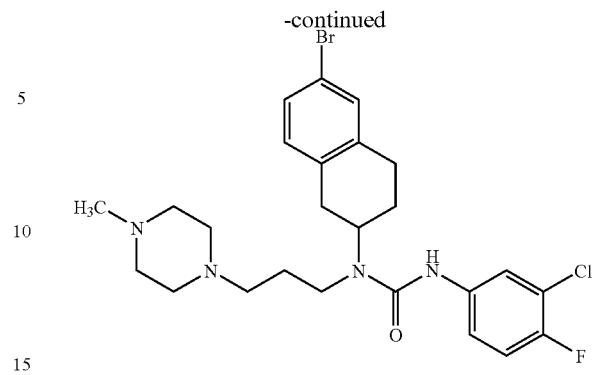

or a pharmaceutically acceptable salt thereof.

16. A compound having the structural formula

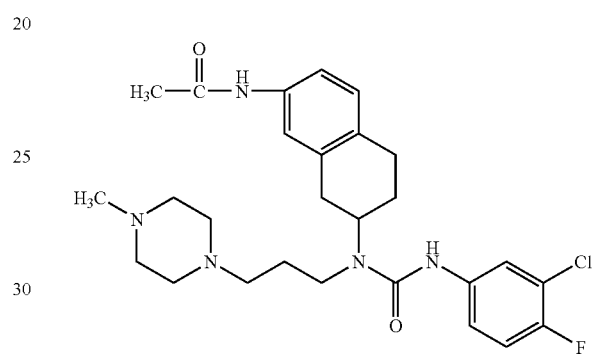

or a pharmaceutically acceptable salt thereof.

17. A pharmaceutical composition comprising a therapeutically effective amount of at least one compound of claim 1 in combination with at least one pharmaceutically acceptable carrier.

18. A pharmaceutical composition comprising a therapeutically effective amount of at least one compound of claim 14 in combination with at least one pharmaceutically acceptable carrier.

19. A pharmaceutical composition comprising a therapeutically effective amount of at least one compound of claim 15 in combination with at least one pharmaceutically acceptable carrier.

* * * * *